US011493510B2

(12) United States Patent
Matsuba et al.

(10) Patent No.: US 11,493,510 B2
(45) Date of Patent: Nov. 8, 2022

(54) DETECTION METHOD USING FIBROUS SUBSTANCE

(71) Applicant: TOSOH CORPORATION, Shunan (JP)

(72) Inventors: Takao Matsuba, Ayase (JP); Ryuji Kobayashi, Ayase (JP); Yu Muto, Ayase (JP); Yasutoshi Kawai, Ayase (JP)

(73) Assignee: TOSOH CORPORATION, Shunan (JP)

( * ) Notice: Subject to any disclaimer, the term of this patent is extended or adjusted under 35 U.S.C. 154(b) by 23 days.

(21) Appl. No.: 16/323,928

(22) PCT Filed: Aug. 4, 2017

(86) PCT No.: PCT/JP2017/028402
§ 371 (c)(1),
(2) Date: Feb. 7, 2019

(87) PCT Pub. No.: WO2018/030295
PCT Pub. Date: Feb. 15, 2018

(65) Prior Publication Data
US 2020/0191783 A1     Jun. 18, 2020

(30) Foreign Application Priority Data

| Aug. 9, 2016 | (JP) | JP2016-156775 |
| Nov. 7, 2016 | (JP) | JP2016-217584 |
| Feb. 2, 2017 | (JP) | JP2017-017706 |
| Apr. 7, 2017 | (JP) | JP2017-077086 |
| May 24, 2017 | (JP) | JP2017-102715 |

(51) Int. Cl.
*G01N 33/543* (2006.01)
*G01N 33/542* (2006.01)

(52) U.S. Cl.
CPC ..... *G01N 33/54393* (2013.01); *G01N 33/542* (2013.01)

(58) Field of Classification Search
None
See application file for complete search history.

(56) References Cited

U.S. PATENT DOCUMENTS

| 4,493,815 A * | 1/1985 | Fernwood | B01D 61/18 210/232 |
| 4,777,021 A * | 10/1988 | Wertz | B01L 3/50255 422/534 |
| 5,091,318 A * | 2/1992 | Anawis | A61K 39/35 436/513 |
| 5,104,790 A * | 4/1992 | Flesher | C07K 14/005 435/339.1 |
| 5,187,067 A * | 2/1993 | Koike | C07K 16/18 435/337 |
| 2005/0019668 A1 * | 1/2005 | Yamamoto | H01B 1/122 429/317 |
| 2006/0286446 A1 * | 12/2006 | Chun | H01M 2/16 429/142 |
| 2007/0298435 A1 | 12/2007 | Aoyagi et al. | |
| 2010/0285972 A1 * | 11/2010 | Dubrow | B82Y 30/00 506/7 |
| 2017/0265788 A1 * | 9/2017 | Quan | A61B 5/14546 |

FOREIGN PATENT DOCUMENTS

| GB | 2181840 A | 4/1987 |
| JP | 2000-279176 A | 10/2000 |
| JP | 2003-322653 A | 11/2003 |
| JP | 2012-047747 A | 3/2012 |
| JP | 2012-140331 A | 7/2012 |
| JP | 2013-529788 A | 7/2013 |
| WO | 02061406 A1 | 8/2002 |
| WO | 2006/011543 A1 | 2/2006 |
| WO | 2010/134592 A1 | 11/2010 |
| WO | 2012/004635 A1 | 1/2012 |

OTHER PUBLICATIONS

Chattopadhyay et al., Sensitivie detection of food-borne pathogen Salmonella by modified PAN fibers-immunoassay, Biosensors and Bioelectronics 45, 2013, pp. 274-280. (Year: 2013).*
Hersey et al., Functionalized Nanofiber Meshes Enhance Immunosorbent Assays, Anal. Chem. 2015, 87, pp. 11863-11870. (Year: 2015).*
International Search Report of PCT/JP2017/028402 dated Nov. 7, 2017.
International Preliminary Report on Patentability and Translation of Written Opinion, dated Feb. 12, 2019 from the International Bureau in counterpart International application No. PCT/JP2017/028402.
Communication dated Feb. 14, 2020 from the European Patent Office in application No. 17839366.6.
Memisevic, J., et al., "Electrospun sol-gel fibers for fluorescence-based sensing", Proceedings of SPIE, vol. 7313, 2009, XP055662537, 9 pages.

* cited by examiner (Continued)

Primary Examiner — Gary Counts
(74) Attorney, Agent, or Firm — Sughrue Mion, PLLC

(57) ABSTRACT

A method for detecting a substance to be detected, which comprises bringing
  a) a first recognizing substance bound to a fibrous substance,
  b) a second recognizing substance which is labeled, and
  c) a substance to be detected,
  provided that the first recognizing substance and the second recognizing substance are capable of being bound to the substance to be detected,
  into contact with one another in a dispersed state so as to form a complex in which the above a, b and c are bound together,
separating the complex and an unbound b, and
detecting the label of the obtained complex.

5 Claims, 15 Drawing Sheets
Specification includes a Sequence Listing.

| | 1 | 2 | 3 |
|---|---|---|---|
| Filter color (visually observed) | White | White | Red |
| Peptide-recognizing antibody-fixed gold colloid | + | + | + |
| Peptide-bound flagella (monomer) | — | + | — |
| Peptide-bound flagella | — | — | + |

Image of peptide-recognizing antibody-fixed gold colloid

Image of peptide-bound flagellum (monomer)

↑ 65°C 15 min

Image of peptide-bound flagellum

Fig. 5

| | 1 | 2 |
|---|---|---|
| | 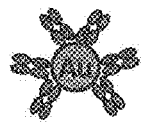 | |
| Filter color (visually observed) | White | Red |
| Peptide-recognizing antibody-fixed gold colloid | + | + |
| Flagella | + | − |
| Peptide-bound flagella | − | + |

| | |
|---|---|
| Image of peptide-recognizing antibody-fixed gold colloid | |
| Image of peptide-bound flagellum |  |
| Image of flagellum |  |

Fig. 6

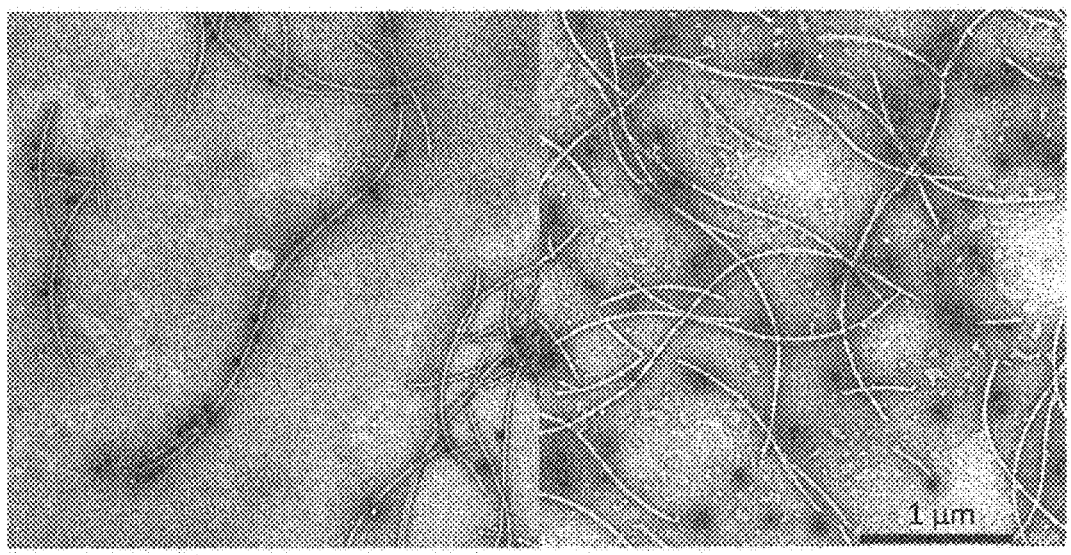

Peptide-bound flagella
+
Peptide-recognizing antibody-fixed gold colloid

Peptide-bound flagella
+
Streptavidin-fixed gold colloid

Fig 7

| Peptide-bound flagella (μg) | 10 | 5 | 2.5 | 1.25 | 0.63 | 0.31 | 0.16 | 0 |
|---|---|---|---|---|---|---|---|---|
| Peptide-recognizing antibody-fixed gold colloid (μl) | 5 | 5 | 5 | 5 | 5 | 5 | 5 | 5 |
| Color (visually observed) Red | ++++++ | +++++ | ++++ | +++ | ++ | + | - | - |
| Color (visually observed) Black | - | + | ++ | +++ | ++++ | +++++ | ++++++ | - |

Image of peptide-recognizing antibody-fixed gold colloid 

Image of peptide-bound flagellum 

Fig 8

| Reaction time (sec) | 15 | 30 | 60 | 120 | 300 |
|---|---|---|---|---|---|
| Color strength (visually observed) | +++ | ++++ | +++++ | +++++ | +++++ |

Image of peptide-recognizing antibody-fixed gold colloid 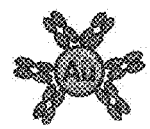

Image of peptide-bound flagellum 

Fig 9
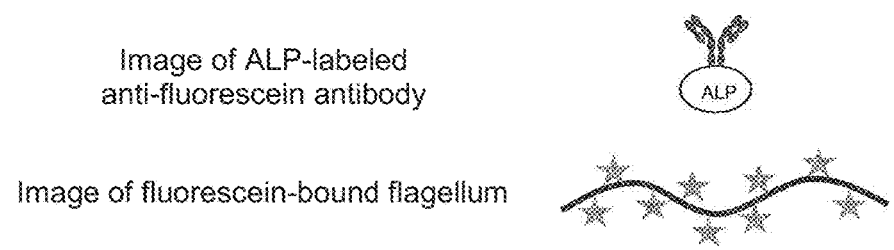
Fig 10
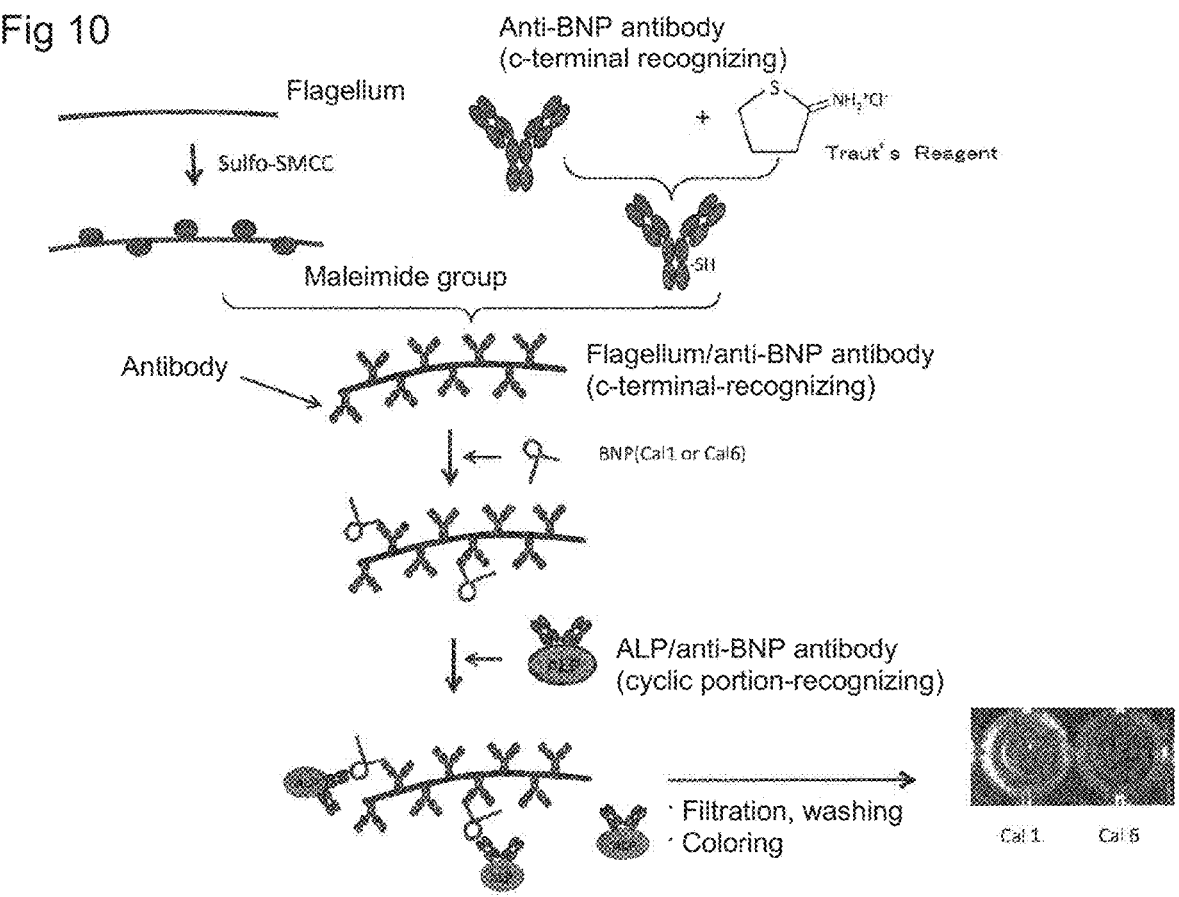

Enlarged view (low concentration region)

cal1 cal6

100 μm

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 1
gtgcaggttc cgcaactgcc aacc                                    24

<210> SEQ ID NO 2
<211> LENGTH: 23
<212> TYPE: DNA
<213> ORGANISM: Artificial Sequence
<220> FEATURE:
<223> OTHER INFORMATION: Synthetic primer sequence

<400> SEQUENCE: 2
aattatcaat ctgaacaggt gta                                     23

DETECTION METHOD USING FIBROUS SUBSTANCE

CROSS REFERENCE TO RELATED APPLICATIONS

This application is a National Stage of International Application No. PCT/JP2017/028402 filed Aug. 4, 2017, claiming priority based on Japanese Patent Application No. 2016-156775 filed Aug. 9, 2016, Japanese Patent Application No. 2016-217584 filed Nov. 7, 2016, Japanese Patent Application No. 2017-017706 filed Feb. 2, 2017, Japanese Patent Application No. 2017-077086 filed Apr. 7, 2017, and Japanese Patent Application No. 2017-102715 filed May 24, 2017.

TECHNICAL FIELD

The present invention relates to a detection system utilizing a fiber for detecting an intermolecular interaction.

BACKGROUND ART

As for an interaction of an antigen and an antibody, it has been known that the reaction rate is high when the antigen and the antibody are uniformly present in a solution. The measurement system which takes the advantage is a homogeneous measurement system, in which the antigen and the antibody reach in an equilibrium state in a very short time after being mixed, whereby the measurement can be started usually in several minutes after mixing the reagents in many cases. Several such measurement systems have been reported, represented by fluorescence resonance energy transfer (FRET). The principle is a phenomenon as follows. A fluorescence spectrum of a certain fluorescent molecule (hereinafter referred to as a donor) and an excitation spectrum of another fluorescent molecule (hereinafter referred to as an acceptor) overlap each other, and when these molecules come very close to each other at several nanometer level, the fluorescence energy of the donor excites the acceptor thereby to generate fluorescence attributable to the acceptor. An explanation will be made with reference to a sandwich assay in which an antigen is sandwiched between two antibodies. In a case where one antibody is labeled with the donor and the other antibody is labeled with the acceptor, when the two labeled antibodies come close to each other via the antigen, energy transfer occurs thereby to generate a fluorescence signal of the acceptor. That is, since the fluorescence signal increases depending upon the amount of the antigen, the amount of the antigen can be determined in a homogeneous system. However, even when no antibody is present, the donor and the acceptor come close to each other with a certain probability, whereby a signal is generated, which corresponds to the background signal.

As one method of reducing background noises, use of an antibody having a very high affinity is considered. According to this method, the antibody concentration in the measurement system can be reduced, and thus the donor and the acceptor are less likely to nonspecifically come close to each other, whereby the background signal will reduce. However, it is not realistic to prepare an ultrahigh affinity antibody which can be used for the measurement system, and even if it can be prepared, it is not possible to reduce the background signal as in the case of a heterogeneous measurement system comprising a step of separating an unbound substance (hereinafter referred to as B/F separation).

Further, a labeling method by which energy transfer between two types of fluorescent substances efficiently occurs when the antibodies come close to each other via an antigen, has not established yet.

DISCLOSURE OF INVENTION

Technical Problem

The homogeneous system has an advantage such as a high reaction rate but has a disadvantage such that the S/N ratio is not high. Accordingly, in the case of a measurement system in which a high S/N ratio is required, a heterogeneous measurement system of conducing B/F separation operation is employed in many cases. This is because a substance which has not involved in the reaction can be removed out of the system by the B/F separation operation, whereby the background signal can be remarkably reduced, thus improving the S/N ratio. For such a system, it is necessary to fix a substance having a binding capacity to an object to be measured (in the following, exemplified as an antibody), e.g. on a water-insoluble carrier. However, if so, the reaction between the object to be measured and the antibody is a solid-liquid reaction, and thus it will take long until equilibrium is achieved as compared with the homogenous reaction.

In order to shorten the reaction time, a method of forming the water-insoluble carrier into fine particles may be mentioned, whereby the dispersibility of the antibody in the solution increases and the reaction rate thereby improves. For example, a method of using magnetic fine particles as the water-insoluble carrier and separating the fine particles by magnetic force may be mentioned. Further, as the particles become finer, the system becomes closer to the homogeneous measurement system, and the reaction rate becomes high, however, simple B/F separation by e.g. magnetic separation becomes difficult, and complicated separation e.g. by centrifugal separation will be required. That is, construction itself of the measurement system is complicated, and such a measurement system can hardly be industrially applicable.

As a result, taking both the antigen-antibody reaction rate and simple B/F separation step into consideration, as the water-insoluble carrier, fine particles at a level of several micrometer to submicron capable of B/F separation in a short time e.g. by magnetic force have been practically used.

As mentioned above, in order to achieve a high reaction rate and easy separation, it is necessary to form the water-insoluble carrier into fine particles at a level of from several micrometer to submicron, however, particles of such a size are opaque. Accordingly, in a case where a labeled substance is detected e.g. by visual observation, absorption, fluorescence or the like, a labeled substance which is hidden by the particles as observed from a detector side can not be detected, and detection particularly in a low concentration region is difficult.

Solution to Problem

In order to achieve high sensitivity measurement in a short time, it is necessary to keep a high S/N ratio and to improve the reaction rate. The former requires to improve the signal value and to reduce noises. The latter requires to bring the system close to the homogeneous reaction as far as possible. Therefore, in order to improve the S/N ratio, various studies have been made on materials capable of B/F separation and materials which have a reaction rate equal to that of the homogeneous reaction and as a result, is has been found to utilize a fibrous substance as a substance on which an antigen-recognizing substance is to be fixed, and the present invention has been accomplished.

That is, the present invention provides the following.

(1) A method for detecting a substance to be detected, which comprises bringing a) a first recognizing substance bound to a fibrous substance, b) a second recognizing substance which is labeled, and c) a substance to be detected provided that the first recognizing substance and the second recognizing substance are capable of being bound to the substance to be detected, into contact with one another in a dispersed state so as to form a complex in which the above a, b and c are bound together, separating the complex and an unbound b, and detecting the label of the obtained complex.

(2) The method according to (1), wherein the fibrous substance is a straight chain fiber.

(3) The method according to (1) or (2), wherein the fibrous substance is a fiber constituted by self-organization or a polymer prepared by electrospinning.

(4) The method according to any one of (1) to (3), wherein the separation is conducted by filtration separation, centrifugal separation or electrophoresis.

(5) The method according to any one of (1) to (4), wherein the recognizing substance is an antibody against the substance to be detected.

Now, the present invention will be described in detail below.

The state of the fibrous substance used in the present invention is not limited so long as it can be present in a dispersed state in a solution even when bound to the first recognizing substance, and it may be a fiber having properties such that it can be present in a dispersed state in a buffer solution commonly used in biochemical experiments such as PBS or TBS or a buffer solution containing proteins. For example, the fibrous substance may be such that the concentration difference between the upper portion and the lower portion of the solution is within 20%, preferably within 10%.

The fibrous substance may be not only one consisting of one straight chain fiber but also one which is branched in the middle, which is bent or which is in a network form. The diameter of the fiber is not necessarily uniform, so long as the fiber has physical properties such that it can be present in a dispersed state in the solution and that it can be separated by e.g. filtration separation. However, many of fibrous substances obtained by fibrillating a natural product contain an irregular branch-like structure in the middle of fibrillation, and if this structure is contained in a large amount, the background signal of the constructed measurement system tends to increase, and accordingly such a structure is preferably reduced to a practically non-problematic level.

It is not clearly understood why such a structure causes the increase of the background signal, and it is estimated that a labeled substance such as gold colloid is trapped by the irregular branches.

From above, a straight chain fiber can be preferably used for this purpose. For example, a fiber constituted by self-organization of a peptide or a protein, or a polymer prepared by electrospinning can also be preferably used for this purpose.

Further, the cross sectional shape of the fiber is not particularly limited, and may be one having a symmetric shape such as a circle, a quadrangle, a rhombus or a star, or may be one not having a definite shape. Further, the respective fibers may be individually present, or a plurality of fibers may be put together, or a plurality of fibers put together may be twisted or formed into a sheet.

The size of the fibrous substance cannot generally be defined since it varies depending upon the shape of the fibrous substance, the protein concentration of the solution used or the type of the buffer solution. For example, in the case of a single straight chain fibrous substance, it may be one having a diameter of from 1 nanometer to several micrometer, preferably from 1 nanometer to 500 nanometer and having a length of from 100 nanometer to 50 micrometer (hereinafter sometimes referred to simply as a nanofiber, or may be one having a ratio of the length to the diameter of the fiber of at least 2, preferably at least 5, further preferably at least 10 and at most 10,000 although the upper limit is not particularly limited.

As the type of the fibrous substance used in the present invention, for example, a protein-based fiber may, for example, be a fiber such as a flagellum, a microtubule, an amyloid fiber, an actin filament, collagen, laminin or gelatin. A fibrous substance other than the protein-based fiber may, for example, be carbon nanofiber, cellulose nanofiber, carboxymethyl cellulose nanofiber, chitin nanofiber or chitosan nanofiber, or a derivative thereof, and a metal fiber of e.g. gold, silver, copper, cobalt or nickel, or a metal oxide fiber of e.g. titanium oxide, zinc oxide, aluminum oxide or tungsten oxide may also be used. Further, a nanofiber prepared by electrospinning may also be used. For example, as an example of a polymer prepared by electrospinning, a method of spinning PVDF, polystyrene, polylactic acid, nylon, polyacrylonitrile, polyvinyl alcohol, polyethylene glycol, polyaniline, polyurethane, polyhydroxybutyrate, polycaprolactone, chitosan, collagen, cellulose or the like by itself, or for the purpose of improving the function, a method of blending a plurality of polymers and spinning them, a method of spinning a copolymer, or a method of spinning a mixture with a material other than a polymer, may be mentioned. Further, a method of spinning different types of polymers from a plurality of nozzles at the same time to prepare a single uniform fiber in a state where the polymers are not mixed with each other may, for example, be mentioned. However, the fibrous substance is not limited thereto. Further, a nanofiber prepared by other method may also be used.

Further, the method for producing the nanofiber is not particularly limited. For example, a method of cultivating and extracting a microorganism, a cultivation method by adding various materials at the time of cultivation, a method of pulverizing a natural material, or a method of chemically growing a material, may, for example, be mentioned.

The recognizing substance may be properly selected in accordance with the reaction system to be constructed. For example, a protein, a peptide, an organic substance, an inorganic substance or a nucleic acid may be used, and as a protein-based recognizing substance, e.g. an antibody is preferably used. As a method of fixing the recognizing substance, the recognizing substance may be bound to the fibrous substance by a chemical bond or via a certain tag. In the case of the former, a reaction between amino groups, a reaction between an amino group and a SH group, or a reaction between an amino group and a carboxy group may, for example, be mentioned, but the method is not limited thereto. Further, fixing via a functional group presented on the fiber surface by a gene engineering means, is also applicable. Further, in the case of the latter, a method utilizing a combination of a tag peptide and a tag-recognizing antibody, or binding property between biotin and avidin may, for example, be mentioned. Otherwise, the fibrous substance may be coated with e.g. a silane coupling agent to modify the surface, to which a recognizing substance such as a protein is bound. Further, in the case of a polymer fiber such as PVDF or PS, the antibody may be fixed to the polymer surface by a hydrophobic bond, or fixation via a functional group on the surface is also possible. In a case where an antibody is bound to the fibrous substance, not only an intact antibody but also a fragment having an antigen binding site remaining, such as $F(ab')_2$, Fab or scFv may be mentioned, but the antibody is not limited to such forms.

The fiber on which the recognizing substance is fixed can be stored e.g. by refrigeration, freezing or freeze drying. On that occasion, as the case requires, various stabilizers or the like may be added.

In the present invention, the first recognizing substance and the second recognizing substance are used, and so long as they can be simultaneously bound to the substance to be detected, they may be the same or different.

The labeled substance may, for example, be gold colloid, a pigment, a fluorescent dye, fine particles, fluorescent fine particles or an enzyme, and such a labeled substance may be detected by a detection method in accordance therewith. Needless to say, a conventional method may be used in combination to improve the sensitivity.

The substance to be detected is not particularly limited and may be an object to be measured by conventional immunoassay. It may, for example, be an antigen, a protein-based substance, or a low molecular weight organic compound, a virus, a bacterium or a cell, but the object is not limited thereto.

In the present invention, first, a) the first recognizing substance bound to the fibrous substance, b) the second recognizing substance which is labeled, and c) the substance to be detected, are brought into contact with one another in a dispersed state in a solution to form a complex in which a, b and c are bound. The order of contact is not particularly limited, and these components may be sequentially brought into contact with one another, or they may be brought into contact with one another simultaneously. Preferably, a and c are brought into contact with each other and bound, unbound c is removed e.g. by filtration separation, and then b is brought into contact, and such a method is preferred in view of excellent sensitivity.

Further, in order to improve dispersibility of the fibrous substance, additives may be added to the detection system. For example, an anionic surfactant, a cationic surfactant, an amphoteric surfactant or an anionic surfactant may be mentioned. Further, it is possible to improve dispersibility of the fibrous substance by adding a protein, polyethylene glycol or the like.

The reaction time between the recognizing substance and the substance to be detected varies depending upon the binding power of the recognizing substance, and the size and the dispersibility of the fibrous substance, and is usually at most 10 minutes, preferably at most 3 minutes, more preferably at most one minute.

Then, a complex in which the above a, b and c are bound, and an unbound b are separated. The separation method is not particularly limited, and filtration separation, centrifugal separation, electrophoresis or the like may be employed. As a method of filtration separation, a filtration membrane may be used. On that occasion, a filtration membrane through which the complex does not pass and the unbound b passes, may be selected. For example, conventional filter paper, a glass fiber, a material such as PVDF, or a filter having a pore size of 0.22, 0.45 or 0.6 micrometer may be mentioned, but the material and the membrane thickness are not particularly limited. As a method of centrifugal separation, the complex and the unbound b can be separated by centrifugal separation at a gravitational acceleration at which the fibrous substance to which the labeled substance is bound settles but the labeled substance does not settle. By electrophoresis, the complex and the unbound b can be separated by a difference in mobility between the fibrous substance to which the labeled substance is bound and the bound substance in a certain electric field.

Then, the label of the separated complex is detected thereby to detect the substance to be detected. The detection may be quantitative or qualitative.

Advantageous Effects of Invention

In the present invention, by converting a water-insoluble carrier into a fibrous substance, as the fibrous substance becomes thin, it can be present in a dispersed state in a solution, and remains dispersed in the solution unless an operation such as centrifugal separation is conducted. Further, since the fibrous substance has a sufficient length in the long axis direction, it can be easily separated e.g. by filtration. That is, by using a fibrous substance, it is possible to construct a measurement system having characteristics which have been considered to be conflicting, such as reaction in a homogeneous system and easy separation. According to the method of the present invention, it is possible to construct a measurement system by which the reaction time is short as compared with a conventional heterogeneous measurement system, and the S/N ratio is high.

BRIEF DESCRIPTION OF DRAWINGS

FIG. 5 is a diagram illustrating reaction (2) between a peptide-bound flagellum and peptide-recognizing antibody-fixed gold colloid.

FIG. 6 is transmission electron micrographs after the reaction (2).

FIG. 7 is a diagram illustrating reaction (3) between a peptide-bound flagellum and peptide-recognizing antibody-fixed gold colloid.

FIG. 8 is a diagram illustrating reaction (4) between a peptide-bound flagellum and peptide-recognizing antibody-fixed gold colloid.

FIG. 9 is a diagram illustrating reaction (1) between a fluorescein-bound flagellum and ALP-labeled anti-fluorescein antibody.

FIG. 10 is a diagram illustrating a sandwich assay of BNP using a fibrous substance.

EXAMPLES

Now, the present invention will be described in further detail with reference to Examples. However, it should be understood that the present invention is by no means restricted to such specific Examples.

Reference Example 1 Preparation of Flagellar Fiber

Figure 1:
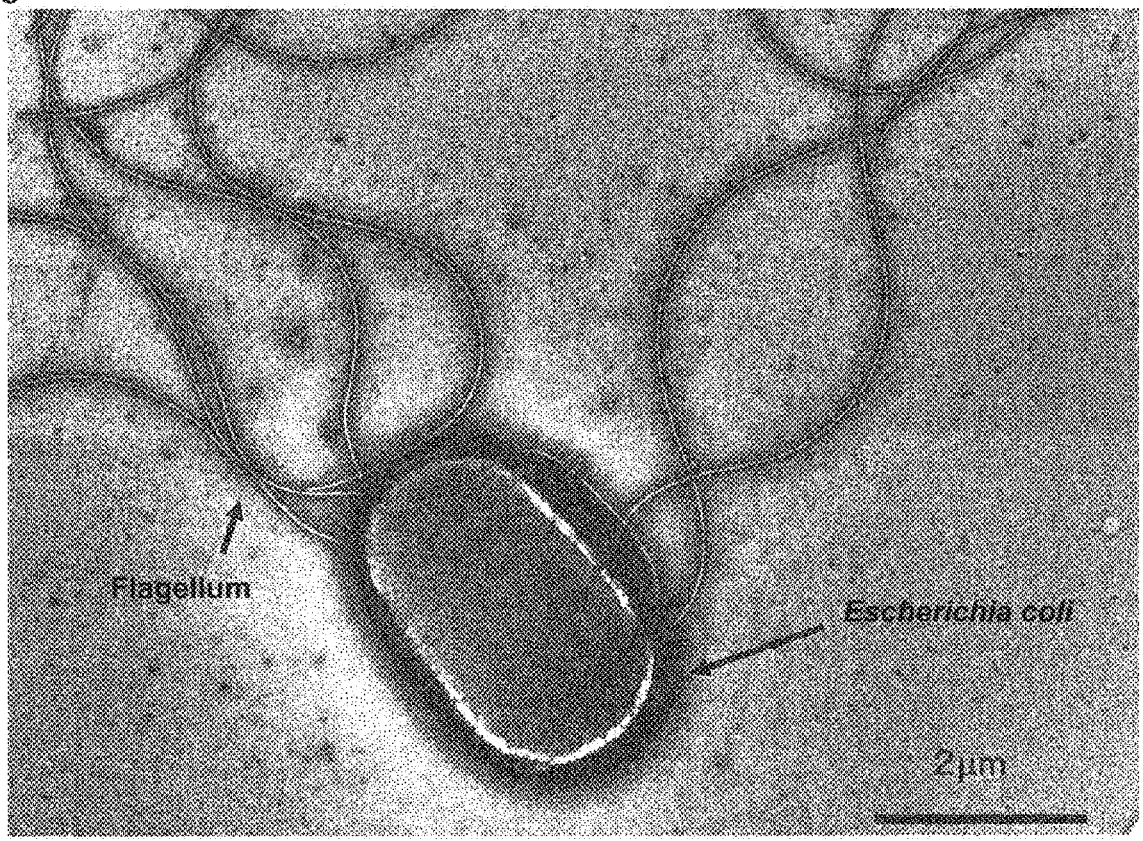
FIG. 1 illustrates *Escherichia coli* developing H48 antigen.
Figure 2:
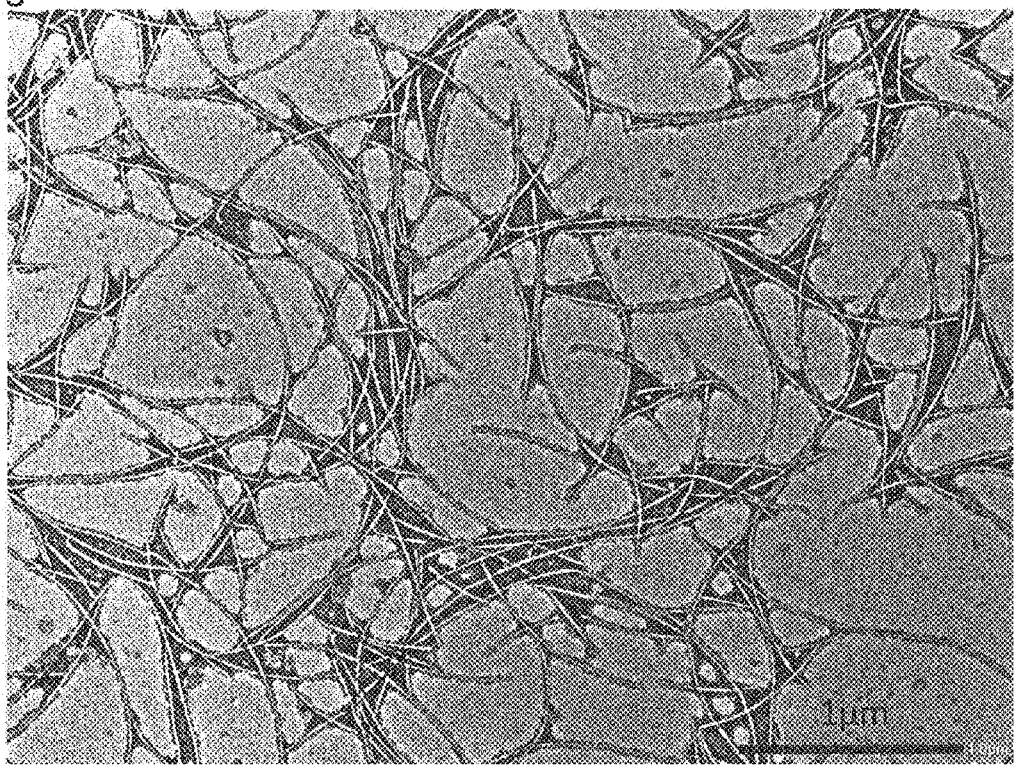
FIG. 2 is an electron micrograph of purified H48 antigen.
Figures 3, 4:
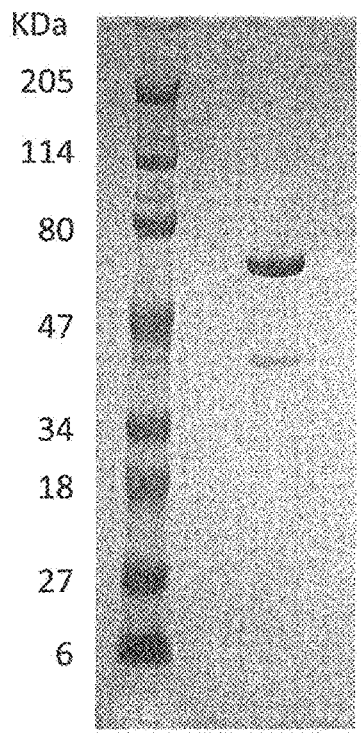
FIG. 3 is a SDS-PAGE photograph of purified H48 antigen.
FIG. 4 is a drawing illustrating reaction (1) between a peptide-bound flagellum and peptide-recognizing antibody-fixed gold colloid.

Flagella were prepared by the method disclosed in JP-A-2000-279176. Briefly speaking, a plasmid having a gene encoding E-coli H48 antibody cloned into pET-19b (manufactured by Novagen), and a plasmid (pPG1-2) having T7-RNA polymerase gene, were introduced into a fliC variant (YK4130) of E-coli K12 strain and cultured in a LB medium containing kanamycin (50 µg/ml) and ampicillin (100 µg/ml) at 30° C. overnight. Then, formation of flagella on E-coli was confirmed by JEM-1400plus (transmission electron microscope, manufactured by JEOL Ltd.) (FIG. 1), and the flagella were recovered as pellets by the method disclosed in JP-A-2000-279176. It was confirmed from a transmission electron micrograph of the flagella and the results of SDS-PAGE that a high purity flagellar fiber was obtained (FIGS. 2 and 3).

Reference Example 2 Peptide Modification of Flagellar Fiber

To 200 µl of the H48 flagella prepared in Reference Example 1 adjusted to 5 mg/ml with PBS, 1 mg of sulfo-SMCC (manufactured by Thermo) was added, followed by reaction at room temperature for one hour. Then, an unreacted reagent was removed by an ultrafiltration membrane Amicon Ultra (manufactured by Millipore) having a molecular cutoff of 100K. 1 mg of the peptide represented by Reference Number 10 disclosed in JP-A-2012-140331 was added, followed by reaction at 4° C. one day. Then, an unreacted peptide was removed by the same ultrafiltration membrane as above to obtain peptide-bound flagella. Further, the peptide-bound flagella were subjected to a heat treatment at 65° C. for 15 minutes to obtain peptide-bound flagella (monomer).

Reference Example 3 Preparation of Peptide-Recognizing Antibody-Fixed Gold Colloid BM33-28 which is an antibody recognizing a cyclic portion of BNP (antibody as disclosed in JP-A-2012-140331) was converted into F(ab')$_2$ form by a conventional method, which was adjusted to 100 µg/ml with distilled water. 1 ml of the antibody solution was added to a solution having 1 ml of a 50 mM phosphate buffer solution having a pH of 7.0 mixed with 9 ml of a 40 nm gold colloid solution (manufactured by BBI Solutions). Then, the mixture was reacted at room temperature for 10 minutes to fix the antibody on the gold colloid. Then, 0.55 ml of 1% polyethylene glycol 20,000 (manufactured by Wako Pure Chemical Industries, Ltd.) and 1.1 ml of a 10% BSA aqueous solution were added, followed by centrifugal separation at 8,000×g for one minute, and gold colloid having the antibody fixed thereon was recovered. The gold colloid was washed several times with a gold colloid storage buffer solution (0.05% PEG20000, 150 mM NaCl, 1% BSA, 0.1% NaN$_3$, 20 mM Tris-HCl buffer solution, pH 8) and diluted with the gold colloid storage buffer solution so that the absorbance at 520 nm would be 6.0, to obtain peptide-recognizing antibody-fixed gold colloid.

Reference Example 4 Reaction of Peptide-Bound Flagella and Peptide Antibody-Fixed Gold Colloid (1)

Each of 100 µg of the peptide-bound flagella and 100 µg of the peptide-bound flagella (monomer) prepared in Reference Example 2 was reacted with the peptide-recognizing antibody-fixed gold colloid (10 µl) prepared in Reference Example 3 at room temperature for 5 minutes and subjecting to filtration through a 0.45 µm Durapore Multiscreen filter (manufactured by Millipore), and the results are shown in FIG. 4. The results obtained by subjecting only the peptide-recognizing antibody-fixed gold colloid (10 µl) to filtration are also shown in FIG. 4.

In the case of the peptide-bound flagella, the color of the gold colloid remained on the filter, whereas in the case of the peptide-bound flagella (monomer) and in a case where only the peptide-recognizing antibody-fixed gold colloid was subjected to filtration, the color of the gold colloid did not remain (white), and thus it was shown that the antibody on the gold colloid surface was bound to the peptide on the flagellum surface and remained on the filter.

Reference Example 5 Reaction of Peptide-Bound Flagella and Peptide Antibody-Fixed Gold Colloid (2)

Each of 50 µg of the peptide-bound flagella prepared in Reference Example 2 and 50 µg of the flagella prepared in Reference Example 1, and 5 µl of the antibody-fixed gold colloid prepared in Reference Example 4 were reacted at room temperature for 5 minutes and subjected to filtration through a 0.6 µm Durapore membrane filter (manufactured by Merck Millipore), and the results are shown in FIG. 5. It was shown from these results that the color of the gold colloid remained on the filter only in a case of the peptide-bound flagella, the gold colloid was bound to the flagellum via the peptide on the flagellum surface, not the gold colloid was entangled in the flagella.

Reference Example 6 TEM Photographing of Reference Example 5

The peptide-bound flagella prepared in Reference Example 2 and the peptide-recognizing antibody-fixed gold colloid prepared in Reference Example 3 or commercially available streptavidin-fixed gold colloid (manufactured by BBI Solutions) were mixed and negatively stained with phosphotungstic acid on a collodion film-bonded mesh (manufactured by Nisshin EM Co., Ltd.), and a transmission electron micrograph was taken by JEM-1400plus (FIG. 6). The left photograph represents the mixture of the peptide-bound flagella and the peptide-recognizing antibody-fixed gold colloid, and the right photograph represents the mixture of the peptide-bound flagella and the streptavidin-fixed gold colloid. It was confirmed from these photographs that the peptide antibody-fixed gold colloid was specifically bound to the surface of the peptide-bound flagella.

Reference Example 7 Reaction of Peptide-Bound Flagella and Peptide Antibody-Fixed Gold Colloid (3)

The antibody-fixed gold colloid (5 µl) prepared in Reference Example 3 and each of various amounts (see numerical values in FIG. 7) of the peptide-bound flagella prepared in Reference Example 2 were reacted at room temperature for 5 minutes and subjected to filtration through a 0.6 µm Durapore membrane filter. As a result, as the amount of the peptide-bound flagella decreases, the color of the gold colloid on the filter changed from red to black (FIG. 7). It is known that the gold colloid changes from red to black as the gold colloidal particles get closer to each other. Thus, it is considered that as the amount of the peptide-bound flagella present in the reaction system decreases, the gold colloid particles bound on the flagella get closer to each other, and thus the gold colloid changes to black. This also confirms binding of the gold colloid to the flagella.

Reference Example 8 Reaction of Peptide-Bound Flagella and Peptide Antibody-Fixed Gold Colloid (4)

The time after 5 µl of the peptide-recognizing antibody-fixed gold colloid prepared in Reference Example 3 and 10 µg of the peptide-bound flagella prepared in Reference Example 2 were mixed until the mixture was subjected to filtration, was variously changed (see numerical values in FIG. 8), and the color of the filter with each reaction time was observed (FIG. 8). As a result, the color of the filter did not substantially change after the reaction time exceeded 60 seconds, and accordingly a measurement system in which the reaction proceeded in a very short time was confirmed.

Reference Example 9 Reaction of Fluorescein-Bound Flagella and ALP-Labeled Anti-Fluorescein Antibody An anti-fluorescein antibody was isolated by a conventional method using as an immunogen albumin having fluorescein bound thereto. Then, in accordance with the directions of LK-12 (manufactured by DOJINDO LABORATORIES) which is an ALP-labeled reagent, an ALP-labeled anti-fluorescein antibody was prepared.

A solution having 1 mg of NHS-fluorescein (manufactured by Thermo) dissolved in 20 µl of DMSO was entirely added to 1 mg of the H48 flagella prepared in Reference Example 1 adjusted to 5 mg/ml with PBS, followed by reaction at room temperature for one hour. Then, an unreacted reagent was removed by an ultrafiltration membrane Amicon Ultra having a molecular cutoff of 100K to obtain fluorescein-bound flagella.

Then, 1 microgram of the fluorescein-bound flagella or the peptide-bound flagella prepared in Reference Example 2, and the ALP-labeled anti-fluorescein antibody (100 µl) diluted 1,000 fold were reacted at room temperature for 5 minutes and subjected to filtration through the same filter as in Reference Example 4. Then, the filter was washed three times with 200 µl of PBS, and a NBT/BCIN reagent (manufactured by Roche) which is a color reagent for ALP was added on the filter, followed by reaction at room temperature for one hour. As a result, the filter colored only at the time of the combination of the fluorescein-bound flagella and the ALP-labeled anti-fluorescein antibody (FIG. 9), which confirmed that flagella to which the ALP-labeled anti-fluorescein antibody was bound was trapped on the filter.

Example 1 Detection of BNP by Antibody-Bound Flagella and ALP-Labeled Antibody (1) Binding of Antibody to Flagella 75 µl of a solution having 1.2 mg of SMCC (manufactured by Thermo) dissolved in 250 µl of DMSO was added to 3 mg of flagella (diameter: about 20 nm, average length: 1.2 µm, straight chain), followed by reaction at room temperature for one hour. Then, an unreacted reagent was removed by the same ultrafiltration membrane having a molecular cutoff of 100K as in Reference Example 2 to prepare flagella having maleimide groups introduced. Then, to 3 mg of BC23-11 (antibody as disclosed in Japanese Patent No. 5810514) which is an antibody recognizing the C terminal of BNP, a solution having 1.2 mg of Traut's Reagent (manufactured by Thermo) dissolved in 250 µl of water was entirely added and left to stand at room temperature for one hour. Then, an unreacted reagent was removed by demineralized column PD-10 (manufactured by GE) to obtain BC23-11 having SH groups introduced. The flagella having maleimide groups introduced and BC23-11 having SH groups introduced were mixed and reacted at room temperature for 3 hours, followed by centrifugal separation at 40,000 rpm for 30 minutes to obtain pellets, which were dissolved in PBS to obtain BC23-11-bound flagella.

(2) Preparation of ALP-Labeled Antibody

BM33-28 converted into F(ab')$_2$ form prepared in Reference Example 3 was ALP-labeled with LK-12.

(3) Detection of BNP

Two sets of BC23-11-bound flagella (10 µg/100 µl PBS) were prepared, and 100 µl each of two types of BNP standard solutions were added respectively. As the BNP standard solutions, Cal1 (BNP 0 pg/ml) and Cal6 (BNP 2420 pg/ml) among BNP standard solutions (manufactured by TOSOH CORPORATION) for AIA reagent were used. The mixtures were reacted at room temperature for one hour and subjected to filtration through the same filter as in Reference Example 4. An operation of adding 200 µl of PBS to conduct filtration washing was carried out three times, 100 µl of ALP-labeled BM33-28 diluted 1,000 fold was added, followed by reaction on the filter at room temperature for one hour, to form a sandwich of the BC23-11-bound flagella and the ALP-labeled BM33-28 via BNP. Then, an operation of adding 200 µl of PBS to conduct filtration washing was carried out three times. Then, 100 µl of the same ALP color reagent as in Reference Example 9 was added, followed by reaction at room temperature for one hour, and the results are shown in FIG. 10. Substantially no coloring was observed in the case of Cal1, whereas deep read coloring was confirmed in the case of Cal6. As mentioned above, it was confirmed that a measurement system in which BNP was sandwiched between two types of antibodies could be constructed on the flagella.

Example 2 Detection of BNP Using Antibody-Bound Flagella and Antibody-Fixed Gold Colloid (1) Binding of Antibody to Flagella In accordance with a conventional method, BM33-28 was subjected to pepsin digestion and reduction to prepare BM33-28 Fab'-form antibody. Then, to 500 µl of the 1 mg/ml flagellum solution (PBS, 10 mM EDTA solution) prepared in Reference Example 1, 6 µl of a DMSO solution of 250 mM SM (PEG) 12 (manufactured by Thermo) was added, followed by reaction at room temperature for one hour. Then, an unreacted reagent was removed by PD-10 (manufactured by GE), 4 mg of the BM33-28 Fab'-form antibody was added, and PBS was added so that the reaction liquid amount would be 1 ml, followed by reaction at room temperature for 2 hours. Then, an unreacted Fab'-form antibody was removed by the same ultrafiltration membrane having a molecular cutoff of 100K used in Reference Example 2 to prepare flagella to which the BM33-28 Fab'-form antibody was bound.

(2) Fixation of Antibody on Gold Colloid

As gold colloid, gold colloid (WRGH1-60NM) having a diameter of 60 nm manufactured by Winered Chemical Corporation was used. To 250 µl of a gold colloid solution, 250 µl of a 10 mM Tris-HCl solution having a pH of 9.2 was added. 500 µl of a 0.1 mg/ml BC23-11 solution (10 mM Tris-HCl) was added thereto and left at rest for 15 minutes. Further, 10 µl of a DMSO solution of 250 mM Methyl-PEG-NHS-Ester (manufactured by Thermo) was added and left at rest for 30 minutes. Sequentially, 1,000 µl of a mixture of BSA and polyethylene glycol 20,000 (manufactured by Wako Pure Chemical Industries, Ltd.) was added and left at rest for 15 minutes. The mixture was subjected to centrifugal separation at 8,000 g for 9 minutes, and a transparent supernatant was disposed of. An operation of adding 1,000 µl of the mixture of BSA and polyethylene glycol 20,000, followed by centrifugal separation was repeatedly carried out. Finally, the pellets were suspended in 300 µl of a buffer solution for gold colloid storage, and the gold colloid solution was diluted with the buffer solution for gold colloid storage so that $OD_{520}$=6.0 to obtain BC23-11-fixed gold colloid.

(3) Detection of BNP

Figure 11:
FIG. 11 is a photograph of a filter after a sample is filtrated (Example 2).
Figure 12:
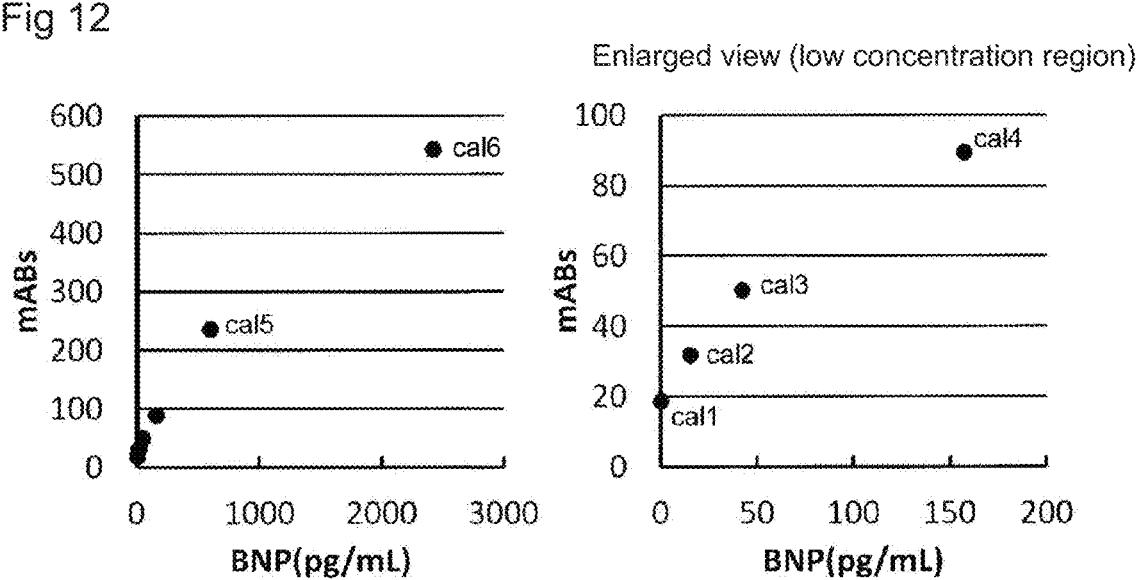
FIG. 12 is a diagram illustrating the strength of a band quantitatively determined by an immunochromatographic reader (Example 2).

Using the above-prepared BM33-28 bound flagella and BC23-11-fixed gold colloid, BNP measurement was carried out as follows. First, 6 sets of a mixture prepared by adding 20 µl of the BC23-11-fixed gold colloid solution to 1 µg of the BM33-28-bound flagella and adjusting the liquid amount to 25 µl with PBS were prepared. Then, 225 µl each of BNP standard solutions for AIA reagent (manufactured by TOSOH CORPORATION) Cal1 to 6 (BNP 0, 15, 42, 157, 599, 2,420 pg/ml) were respectively added and left at rest for 5 minutes. Then, using Bio-dot SF apparatus (manufactured by Bio-Rad Laboratories, Inc.), suction filtration through a 0.65 µm Durapore membrane filter was carried out. The state of the gold colloid remaining on the membrane is shown in FIG. 11. Further, the color strength by the gold colloid on the membrane was measured by an immunochromatographic reader C10066 (manufactured by Hamamatsu Photonics K.K.), and the results are shown in FIG. 12. It was confirmed that the color strength attributable to the gold colloid increases in accordance with the BNP concentration. Thus, it is shown that a system capable of visually detecting a sandwich assay of BNP can be constructed.

Example 3 Detection of BNP Using Antibody-Bound Cellulose and Antibody-Fixed Gold Colloid (1) Binding of Antibody to Cellulose 2 ml of a 2% cellulose (diameter about 0.65 µm, length: about 4.8 µm) solution (manufactured by SUGINO MACHINE LIMITED) was subjected to centrifugal separation at 100×g for 5 minutes, and the obtained supernatant was subjected to centrifugal separation at 15,000 rpm for 5 minutes, and the resulting precipitates were recovered. A 5% solution of trimethoxy(3,3,3-trifluoropropyl)-silane (manufactured by Tokyo Chemical Industry Co., Ltd.) was prepared with a 70% ethanol aqueous solution (pH 3.7), and 1 ml of the solution was added to the precipitates obtained by centrifugal separation, followed by reaction at room temperature for 2 hours. Then, the reaction mixture was subjected to centrifugal separation at 15,000 rpm for 5 minutes, and the precipitates were recovered. The precipitates were washed with ethanol twice and dried (70° C., 3 hours). The dried product was suspended in 500 µL of a 0.2 mg/ml BM33-28 solution (50 mM sodium carbonate buffer, pH 8.5), followed by reaction at 4° C. overnight. 1 ml of PBS was added, and the mixture was subjected to centrifugal separation at 15,000 rpm for 5 minutes, and the resulting precipitates were recovered. Washing with PBS was carried out twice, and the precipitates were suspended in 500 µl of PBS to obtain cellulose having BM33-28 fixed thereon.

(2) Fixation of Antibody on Gold Colloid

The BC23-11-fixed gold colloid prepared in Example 2 was used.

(3) Detection of BNP

Figure 13:
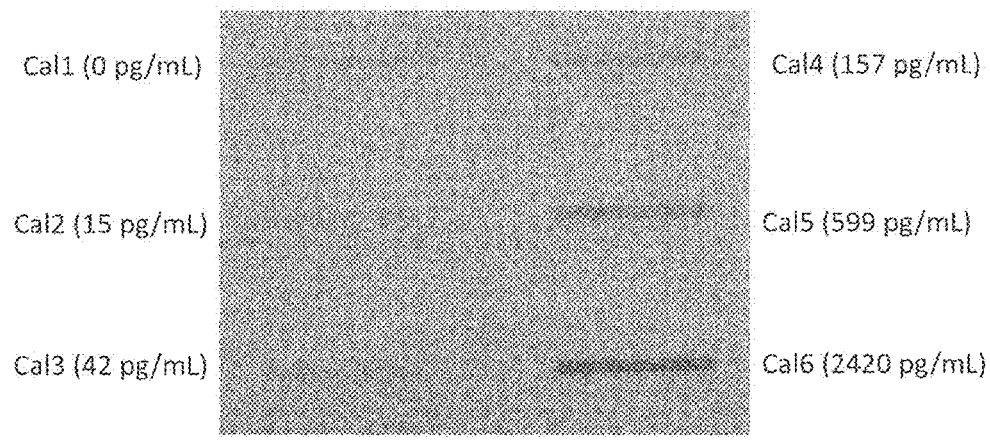
FIG. 13 is a photograph of a filter after a sample is filtrated (Example 3).
Figure 14:
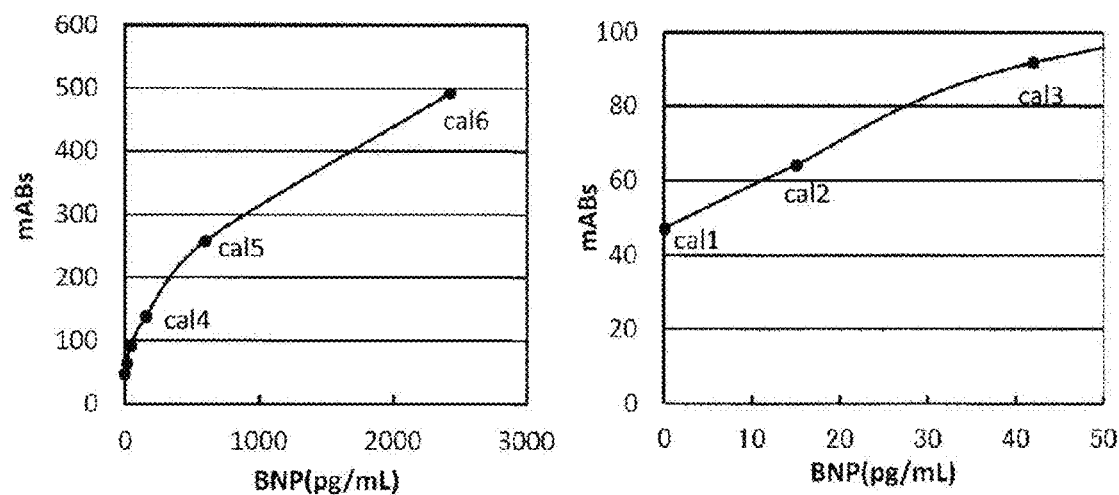
FIG. 14 is a diagram illustrating the strength of a band quantitatively determined by an immunochromatographic reader (Example 3).

6 Sets of a mixture having 20 µl of the BC23-11-fixed gold colloid solution added to 20 µl of the BM33-28-bound cellulose diluted 5 fold with PBS were prepared. Then, 210 µl each of the same BNP standard solutions as in Example 2 were respectively added and left at rest for 5 minutes. Then, using Bio-dot SF apparatus, suction filtration through a 0.65 µm Durapore membrane filter was carried out. The state of the gold colloid remaining on the membrane is shown in FIG. 13. Further, the color strength by the gold colloid on the membrane was measured by an immunochromatographic reader, and the results are shown in FIG. 14. It was confirmed that the color strength attributable to the gold colloid increases in accordance with the BNP concentration. Thus, it was shown that a system capable of visually detecting a sandwich assay of BNP using cellulose fibers can be constructed.

Example 4 Detection of BNP Using Antibody-Bound Chitosan (Diameter: About 0.4 µm, Length: About 3.5 µm) and Antibody-Fixed Gold Colloid (1) Conversion of Amino Group of Chitosan to Thiol Group First, chitosan was suspended in a 1 ml PBS solution at a concentration of 0.05% (weight/volume). Then, the solution was subjected to centrifugal separation at 15,000 rpm for 5 minutes, and chitosan was recovered as pellets. Then, to the pellets, 1 ml of an acidic Traut's solution (100 mM $CH_3COONa$, 2 mg/ml 2-iminothiolane hydrochloride, pH 5.0) was added, followed by sonication and by reaction at room temperature for one hour. After the reaction, to the solution, 200 µl of a neutralizing solution (1M tris(hydroxymethyl)-aminomethane, 100 mM Gly, CI, pH 8) was added, followed by centrifugal separation at 15,000 rpm for 5 minutes.

1 ml of a PBS solution was added to the chitosan in the form of pellets, followed by sonication and by centrifugal separation at 15,000 rpm for 5 minutes. This washing operation with PBS was carried out totally 3 times, and to the chitosan in the form of pellets, 1 ml of 100 mM $CH_3COONa$ (pH 5) was added. In such a manner, chitosan having amino groups converted to thiol groups was prepared.

(2) Introduction of Maleimide Group to Antibody 1 mg of BC23-11 was adjusted to have a concentration of 1 mg/ml in a PBS solution. Then, SM(PEG12) was dissolved in dimethyl sulfoxide at a concentration of 250 mM, and 1 µl thereof was added to the antibody solution. The solution was reacted at room temperature for one hour, and a 1M Tris-HCl buffer solution (pH 8) was added to terminate the reaction. Then, 600 µl of this antibody solution was made to pass through PD-10 column (manufactured by GE), and the buffer was changed to 100 mM $CH_3COONa$ (pH 5). The eluate from the column was concentrated to 500 µl by an ultrafiltration membrane having a molecular cutoff of 30,000 to obtain an antibody having maleimide groups introduced.

(3) Binding of Antibody to Chitosan

500 µl of the chitosan solution having amino groups converted to thiol groups and 500 µl of the antibody solution having maleimide groups introduced were mixed and reacted at 4° C. for one day. Then, the reaction liquid was neutralized with 200 µl of a 1M Tris-HCl buffer solution (pH 8). This solution was subjected to centrifugal separation at 15,000 rpm for 5 minutes, and chitosan having the antibody bound thereto was recovered as pellets. To the pellets, 1 ml of a PBS solution was added, followed by sonication and by centrifugal separation at 15,000 rpm for 5 minutes to wash the antibody-bound chitosan. This washing operation was carried out totally 3 times, and the antibody-bound chitosan was suspended in 500 µl of a PBS solution, followed by sonication. This solution was taken as BC23-11-bound chitosan.

(4) Sensitization of Gold Colloid by Antibody

To 4.5 ml of a gold colloid (manufactured by BBI Solutions) having a diameter of 40 nm, 500 µl of a 50 mM $KH_2PO_4$ (pH 7) solution was added. Then, to this solution, 500 µl of 30 µg/ml BM33-28 was added so as to sensitize the gold colloid at room temperature for 10 minutes. To this solution, 275 µl of a 1% PEG20000 solution and 550 µl of a 10% BSA solution were added, followed by centrifugal separation at 8,000 g at 10° C. for 15 minutes. After the centrifugal separation, the resulting supernatant was disposed of, and the pellets were suspended in a 1 ml gold colloid storage solution. The resulting solution was subjected to centrifugal separation at 8,000 g at 10° C. for 15 minutes, and the gold colloid was recovered as pellets. The pellets were suspended in 1 ml of a gold colloid storage solution, followed by centrifugal separation at 8,000 g at 10° C. for 15 minutes. To the resulting pellets, 500 µl of a gold colloid storage solution was added to obtain BM33-28-sensitized gold colloid.

(5) Detection of BNP

Figure 15:
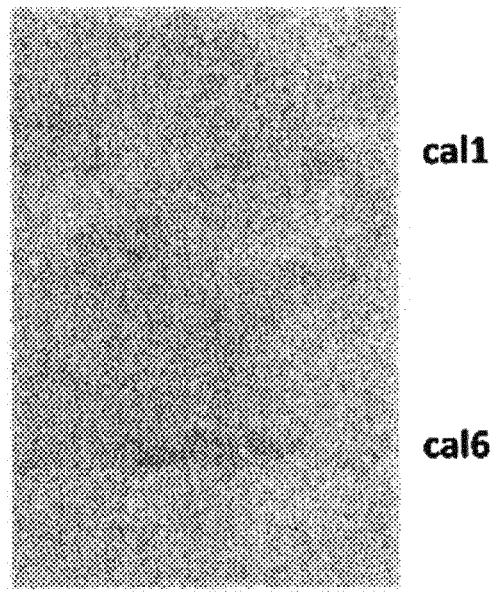
FIG. 15 is a photograph of a filter after a sample is filtrated (Example 4).
Figure 16:
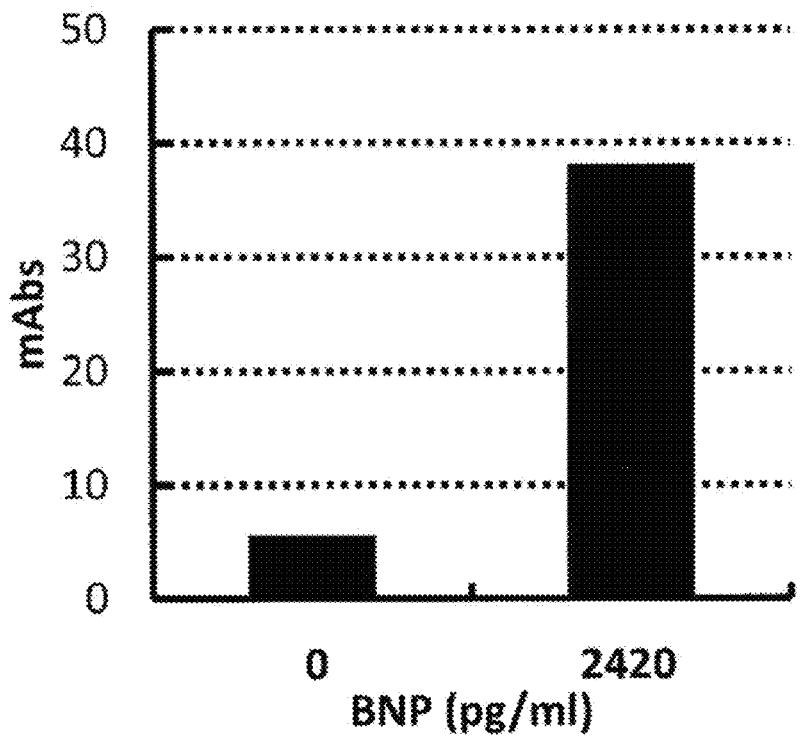
FIG. 16 is a diagram illustrating the strength of a band quantitatively determined by an immunochromatographic reader (Example 4).

To 200 µl of the same BNP calibrator solution as in Example 2, 10 µl of the BM-33-28-sensitized gold colloid was added. To this solution, 1 µl of the BC23-11-bound chitosan was added, followed by well stirring. The solution was left at rest at room temperature for 5 minutes and then subjected to filtration through a Durapore membrane filter having a pore size of 0.65 µm. After the filtration, the membrane was recovered, and the portion at which the calibrator solution passed was photographed (FIG. 15). Further, this position was cut out by scissors, and the strength of the band was quantitatively determined by an immunochromatographic reader. As a result of the experiment, it was confirmed that a band appeared on the membrane by the presence pf BNP (FIG. 16).

Example 5 Detection of BNP Using Antibody-Fixed Cysteine-Substituted Flagella and Antibody-Fixed Gold Colloid (1) Preparation of Cysteine-Substituted Flagella A variant having one amino acid of E-*coli* H48 antigen substituted by cysteine was prepared by a genetic engineering technique. First, using the plasmid having a gene encoding H48 antigen used in Reference Example 1 as a template, by inverse PCR by a pair of forward primer sequence GTGCAGGTTCCGCAACTGCCAACC (SEQ ID NO: 1) and reverse primer sequence AATTATCAATCT-GAACAGGTGTA (SEQ ID NO: 2), a plasmid encoding variant H48-T291C having 291st threonine of H48 antigen substituted by cysteine was constructed.

Figure 17:
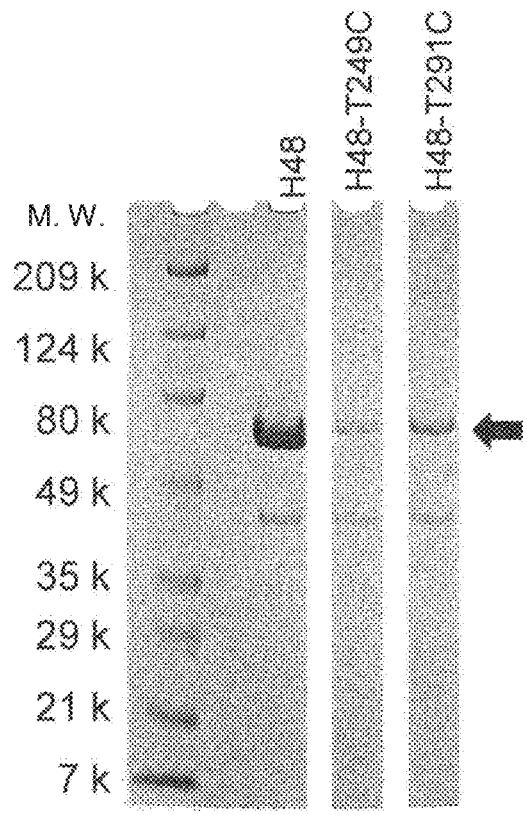
FIG. 17 is a SDS-PAGE photograph of purified cysteine-substituted flagella (Example 5).
Figure 18:
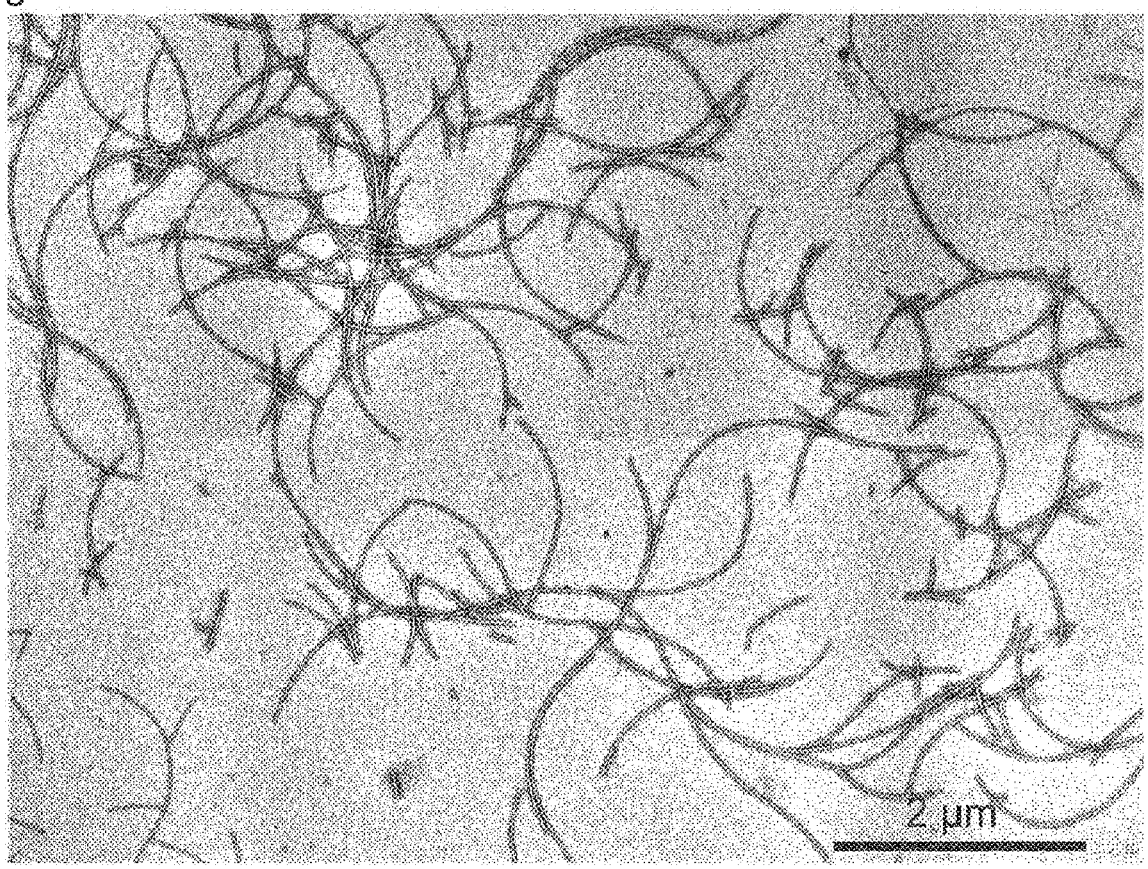
FIG. 18 is a transmission electron micrograph of purified cysteine-substituted flagella (Example 5).

Then, by the method shown in Reference Example 1, the cysteine-substituted flagellar fiber was recovered. The recovered flagella were analyzed by SDS-PAGE under non-reducing conditions, and it was confirmed that the flagellar fiber was isolated with high purity (FIG. 17). Further, the recovered flagellar were observed by a transmission electron microscope and confirmed to have a flagellar structure (FIG. 18).

(2) Fixation of Antibody on Cysteine-Substituted Flagellar

Figure 19:
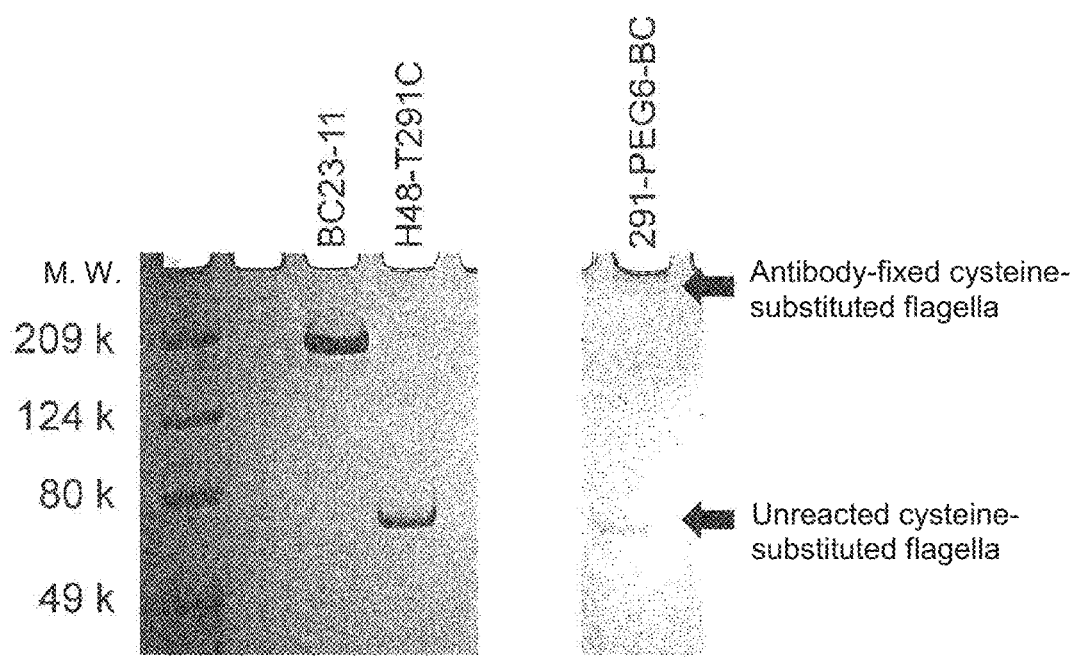
FIG. 19 is a SDS-PAGE photograph of a product obtained by fixing an antibody to cysteine-substituted flagella (Example 5).

180 μg of BC23-11 was adjusted with PBS to a concentration of 5.0 mg/mL, and 6 nmol of SM(PEG) 6 (manufactured by Thermo) was added, followed by reaction at room temperature for one hour. Then, an unreacted reagent was removed by Zeba Spin Desalting Columns (manufactured by Thermo) to obtain an antibody having maleimide groups introduced. Then, 45 μg of the maleimide group-introduced antibody was mixed with 45 μg of the cysteine-substituted flagella, followed by reaction at room temperature for 30 minutes. Then, dialysis for 12 hours with PBS in an amount of 1,000 times the amount of the sample solution using a dialysis membrane (manufactured by Spectrum) having a molecular cutoff of 1000K was carried out five times to remove the unreacted maleimide group-introduced antibody. The obtained product was analyzed by SDS-PAGE under non-reducing conditions, and it was confirmed that the aimed antibody-fixed flagella 291-PEG6-BC were obtained (FIG. 19).

(3) Preparation of Gold Colloid Having Antibody Fixed

BM33-28-fixed gold colloid Au70-BM(Fab') was prepared by the method disclosed in Example 2. As the antibody, Fab' fragmented antibody obtained by pepsin digestion and partial reduction with 2-mercaptoethane was used. As the gold colloid, WRGH1-70NM having a particle size of 70 nm (manufactured by Winered Chemical Corporation) was used.

(4) Detection of BNP

Figure 20:
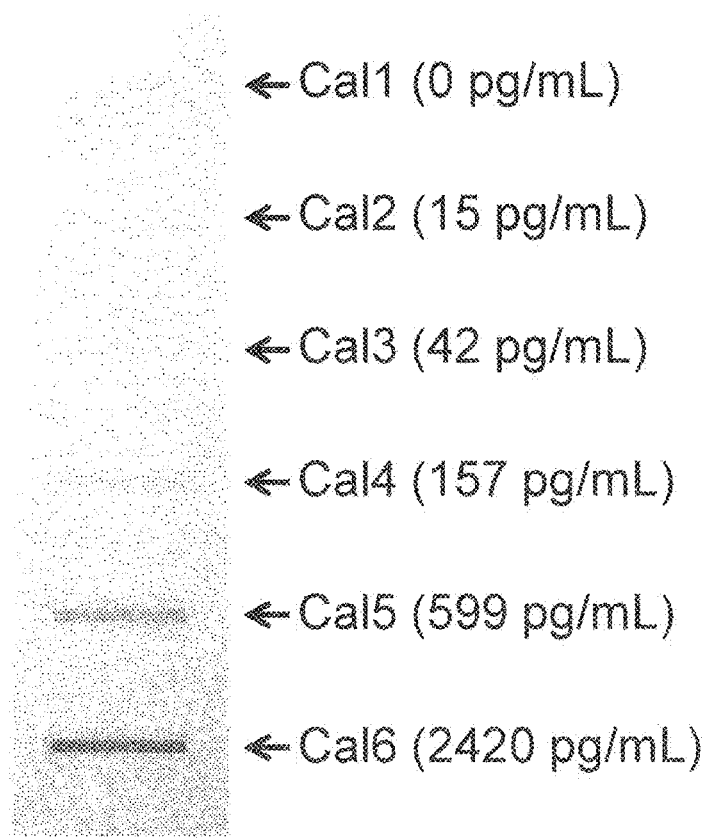
FIG. 20 is a photograph of a membrane filter after detection of BNP differing in the concentration is carried out using antibody-fixed flagella and antibody-fixed gold colloid (Example 5).
Figure 21:
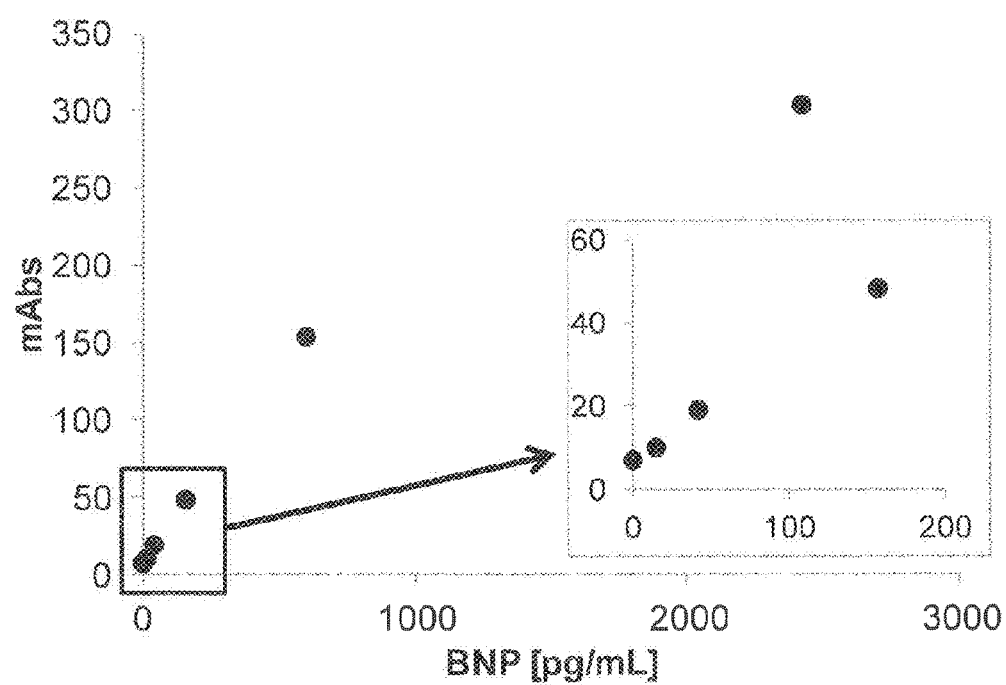
FIG. 21 is a diagram illustrating a relation between the concentration of BNP and the absorbance of gold colloid on the membrane filter (Example 5).

A sandwich assay of BNP was carried out by the following method, using the antibody-fixed flagella 291-PEG6-BC prepared in (2) and the antibody-fixed gold colloid Au70-BM(Fab') prepared in (3). As a measurement sample, the BNP standard solutions used in Example 2 were used. First, 8 μL of the antibody-fixed flagella adjusted to a concentration of 0.4 mg/mL, 8 μL of the antibody-fixed gold colloid adjusted to a concentration so that $OD_{520}$=6.0, and 100 μL of the measurement sample were mixed and left at rest at 37° C. for 30 minutes for reaction. Then, using Bio-dot SF apparatus, suction filtration through a Durapore membrane filter having a pore size of 0.65 μm was carried out, and coloring of the gold colloid remaining on the membrane filter was observed (FIG. 20). Further, the absorbance by the gold colloid was measured by an immunochromatographic reader (FIG. 21). As a result, it was confirmed by visual observation and by measurement of absorbance that the higher the BNP concentration in the measurement sample, the higher the absorbance by the gold colloid on the membrane filter.

Example 6 Detection of BNP Using Antibody-Bound Collagen and Antibody-Bound Gold Colloid (1) Introduction of Maleimide Group to Jellyfish Collagen To 600 μl of jellyfish collagen (manufactured by Jellyfish Research Laboratories, Inc.) adjusted to 1 mg/ml with PBS, 24 μl of a DMSO solution of 250 mM SM(PEG)12, followed by reaction at room temperature for one hour, and 76 μl of a 1M Tris-HCl buffer solution (pH 8.0) was added to terminate the reaction. After the reaction, the reaction mixture was made to pass through PD-10 column (manufactured by GE) equilibrated with a PBS solution to remove an unreacted reagent thereby to obtain collagen having maleimide groups introduced.

(2) Conversion of Amino Group of Antibody to Thiol Group

To 2 ml of BC23-11 adjusted to 1 mg/ml with PBS, 44 μl of Traut's Reagent adjusted to a 2 mg/ml PBS solution was added, followed by reaction at room temperature for one hour, and then 456 μl of a 1M Tris-HCl buffer solution (pH 8.0) containing 100 mM glycine was added to terminate the reaction. After the reaction, the reaction mixture was made to pass through PD-10 column equilibrated with a PBS solution to remove an unreacted reagent. In such a manner, amino groups of the antibody were converted to thiol groups.

(3) Labeling of Jellyfish Collagen with Antibody

The collagen having maleimide groups introduced and the antibody having amino groups converted to thiol groups were mixed and reacted at 4° C. for one day. Then, the solution was put in a 1000 k cut dialysis membrane (manufactured by spectrum) to conduct dialysis with a PBS solution thereby to remove an antibody not labeled with collagen. In such a manner, antibody-labeled collagen was prepared.

(4) Sensitization of Gold Colloid with Antibody

To 4.5 ml of a gold colloid (manufactured by BBI Solutions) solution having a diameter of 40 nm, and 500 μl of a 50 mM $KH_2PO_4$ (pH 7) solution was added. Then, 500 μl of a 30 μg/ml BNM33-28 aqueous solution was added to sensitize the gold colloid at room temperature for 10 minutes. To the resulting solution, 275 μl of a 1% PEG2000 solution and 550 μl of a 10% BSA solution were added, followed by centrifugal separation at 8,000 g at 10° C. for 15 minutes. The pellets obtained after the centrifugal separation were suspended in 1 ml of a gold colloid storage solution. The solution was subjected to centrifugal separation at 8,000 g at 10° C. for 15 minutes, and the gold colloid was recovered as pellets. The pellets were suspended in 1 ml of a gold colloid storage solution, followed by centrifugal separation under the same conditions. To the resulting pellets, 500 μl of a gold colloid storage solution was added to obtain BNM33-28-sensitized gold colloid.

(5) Detection of BNP

Figure 22:
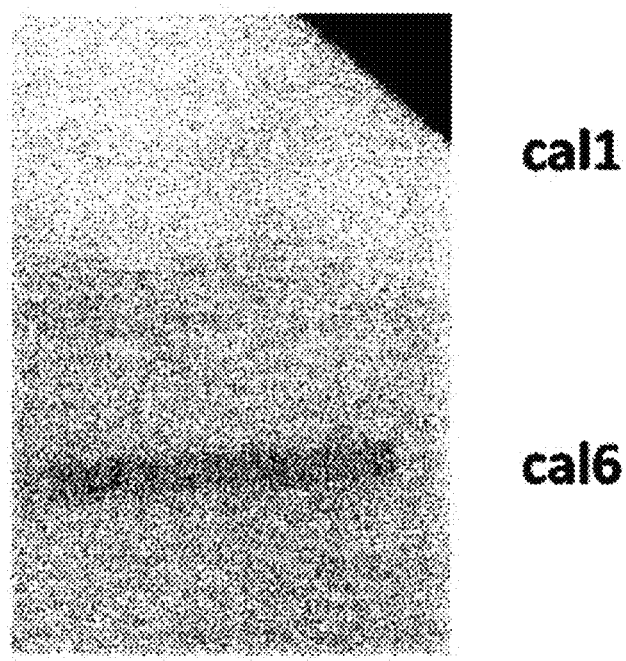
FIG. 22 is a photograph of a filter after a sample is filtrated (Example 6).
Figure 23:
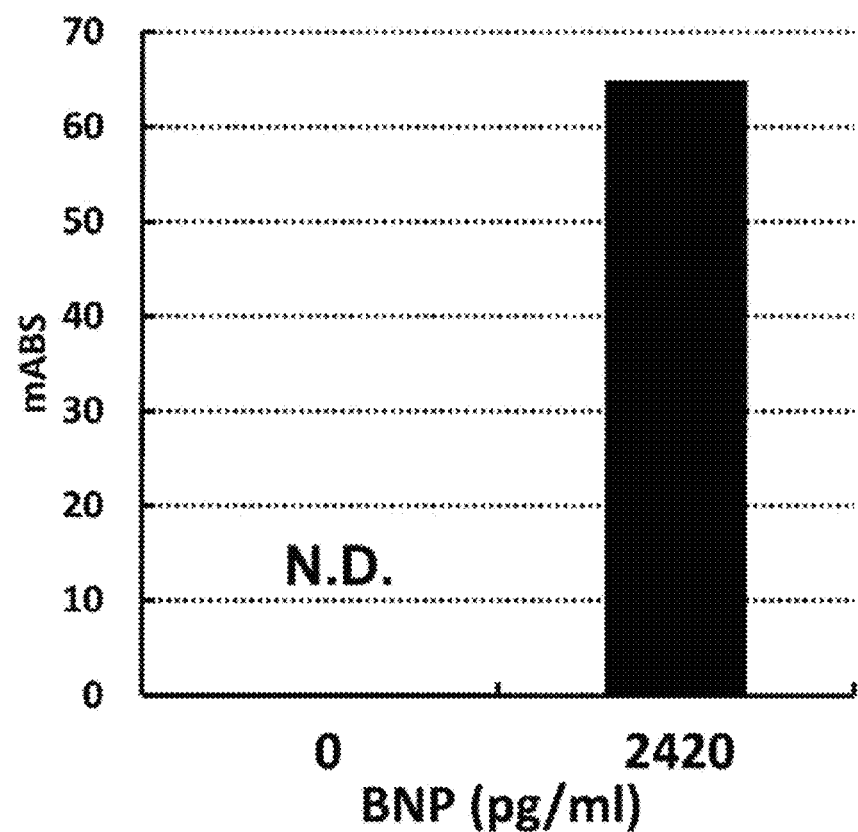
FIG. 23 is a diagram illustrating the strength of a band quantitatively determined by an immunochromatographic reader (Example 6).

To 200 μl of the same calibrator as in Example 1, 10 μl of the BNM33-28-sensitized gold colloid was added, and then 20 μl of the BC23-11-labeled collagen was added, followed by well stirring. The solution was left at rest at room temperature for 5 minutes and subjected to filtration through a Durapore membrane filter having a pore size of 0.65 μm (FIG. 22). Further, the strength of the band was quantitatively determined by an immunochromatographic reader. As a result of the experiment, it was confirmed that a band appeared on the membrane by the presence of BNP (FIG. 23).

Example 7 Detection of BNP by Centrifugal Separation

The BM33-28-bound flagella prepared in Example 2 and ALP-labeled BC23-11 prepared by using LK-12 were used.

Figure 24:
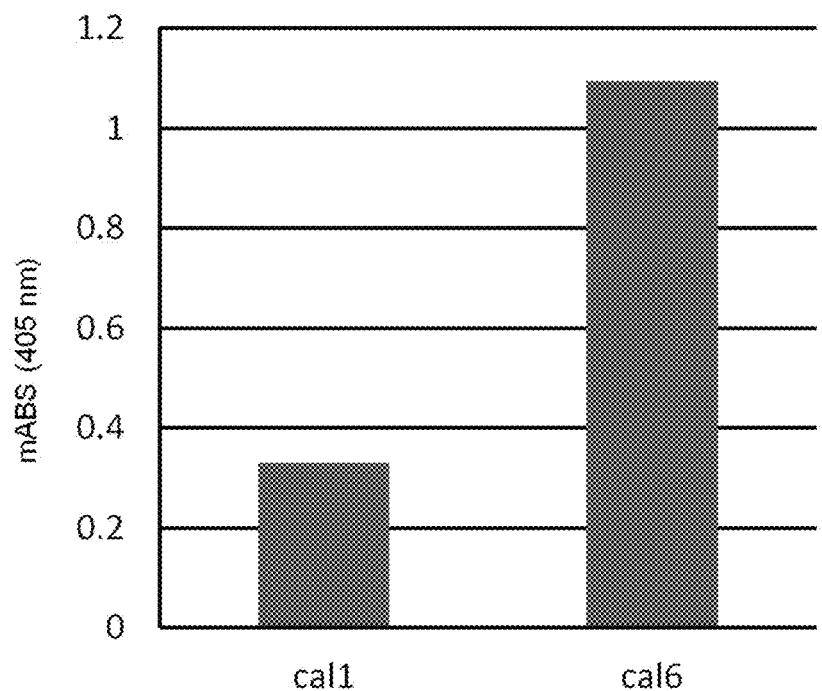
FIG. 24 illustrates results of measurement of the absorbance by a spectrophotometer (Example 7).

Two sets of a solution obtained by adding 300 μl of BC23-11-ALP diluted 1,000 fold with PBS to 10 μg of BM33-28-bound flagella were prepared. 300 μl of the same BNP standard solutions as in Example 1 were respectively added and left at rest for 15 minutes. Each mixture was subjected to centrifugal separation at 40,000 rpm for 30 minutes to precipitate a complex of the BM33-28-bound flagella and BC23-11ALP via BNP. The supernatant was removed, and the precipitates were suspended in 1 ml of PBS, followed by centrifugal separation under the same conditions, and the precipitates were recovered, whereby unreacted BC23-11-ALP was removed. Such an operation was repeated twice. Then, 1 ml of a 1 mg/ml p-nitrophenyl phosphate (pNPP) solution (1M diethanolamine, 0.5 mM $MgCl_2$) was added, and 30 minutes later, the absorbance at 405 nm was measured. The results are shown in FIG. 24. It was confirmed from the results that the absorbance attributable to the substrate increased by the presence of BNP. From the above results, a complex of the BM33-28-bound flagella and BC23-11-ALP via BNP, and BC23-11-ALP which was not formed into a complex, can be separated by centrifugal separation, and thus it was shown that centrifugal separation can be employed as a method for detecting a complex.

Example 8 Detection of BNP Using Electrophoresis

Figure 25:
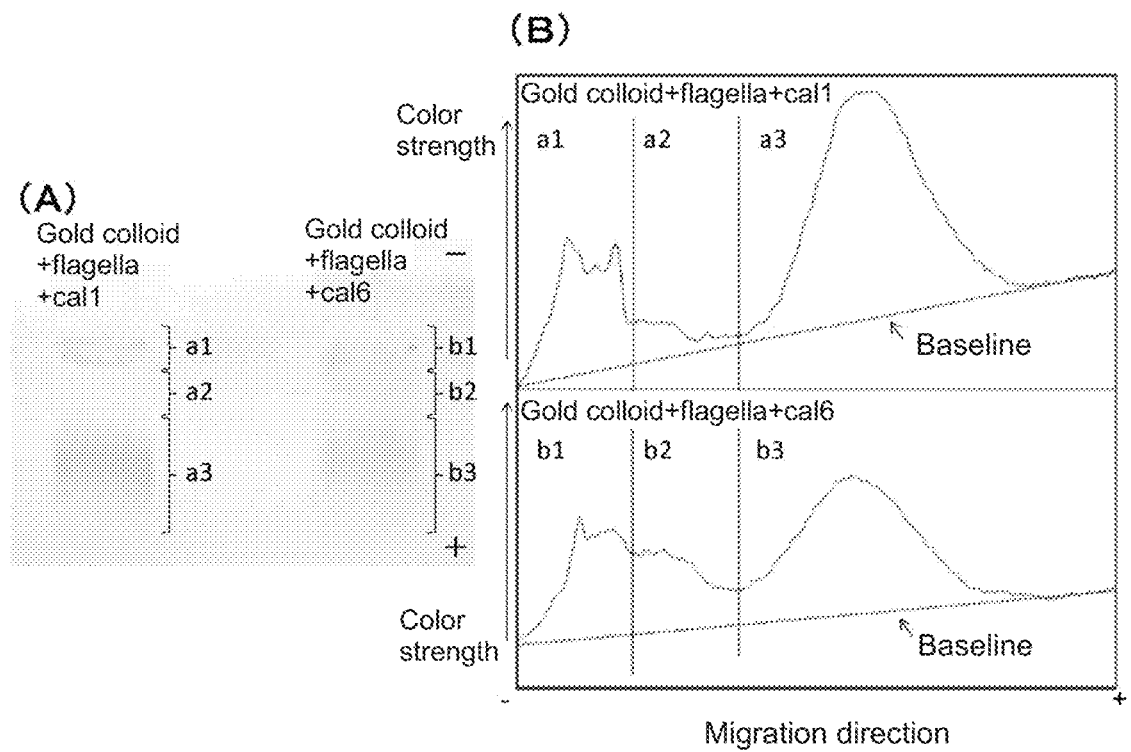
FIG. 25 is a photograph of a gel after agarose electrophoresis and analysis results thereof (Example 8).

Two sets of a solution obtained by mixing 3 μg of the BM33-28-bound flagella and 20 μl of BC23-11-fixed gold colloid, prepared in Example 2, and adjusting the liquid amount to 30 μl with PBS, were prepared. Then, 20 μl each of the same BNP standard solutions as in Example 1 were respectively added and left at rest for 5 minutes. Then, using 0.7% agarose gel, the mixture was subjected to electrophoresis by an electrophoresis apparatus (Mupid-exu, manufactured by ADVANCE) at 135 V for 30 minutes (TAE buffer solution). The photograph of the gel is shown in FIG. 25A. Since the gold colloid is relatively charged, it migrates to the positive side when a voltage is applied. A complex of the BC23-11 gold colloid, BNP and BM33-28-bound flagella can hardly migrate in the agarose gel since its molecules are large, and its migration length is short as compared with the BC23-11-gold colloid which was not formed into a complex. In FIG. 25A, a1 and b1 represent a well portion of the agarose gel, a2 and b2 represents a portion colored by the gold colloid attributable to the complex, and a3 and b3 represent a portion colored by the BC23-11 gold colloid which is not formed into a complex. FIG. 25B illustrates results obtained by treating the image of FIG. 25A by an image analysis software (ImageJ). It is found by the comparison between a2 and b2 that the color strength attributable to the gold colloid is stronger at b2 indicating the result of the electrophoresis in the presence of BNP. The areas of a2 and b2 obtained by imageJ are such that a2: 2955 and b2: 7860, and from the results also, it is found that the migration length by electrophoresis of the gold colloid is shortened by the formation of the complex.

It was shown from the above results that the complex of the BM33-28-bound-flagella and the BC23-11-fixed gold colloid via BNP, and the BC23-11-fixed gold colloid which was not formed into a complex, can be separated by agarose gel electrophoresis.

Figure 26:
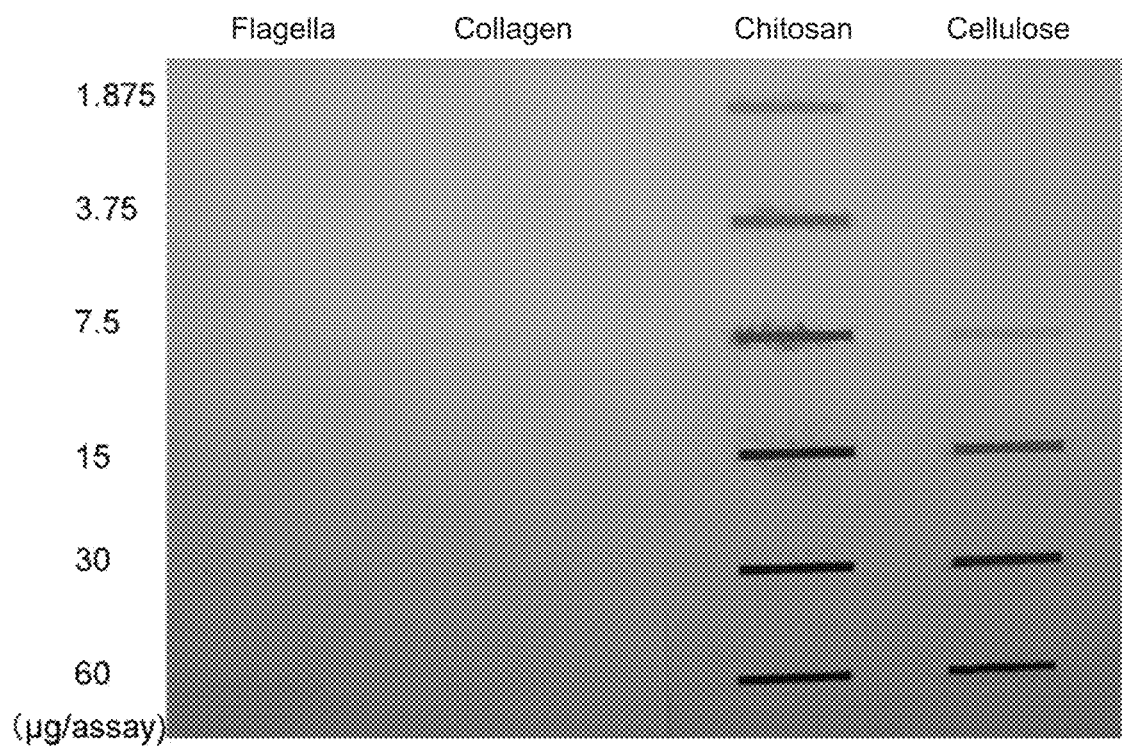
FIG. 26 is a photograph of a filter after a sample is filtrated (Example 9).
Figure 27:
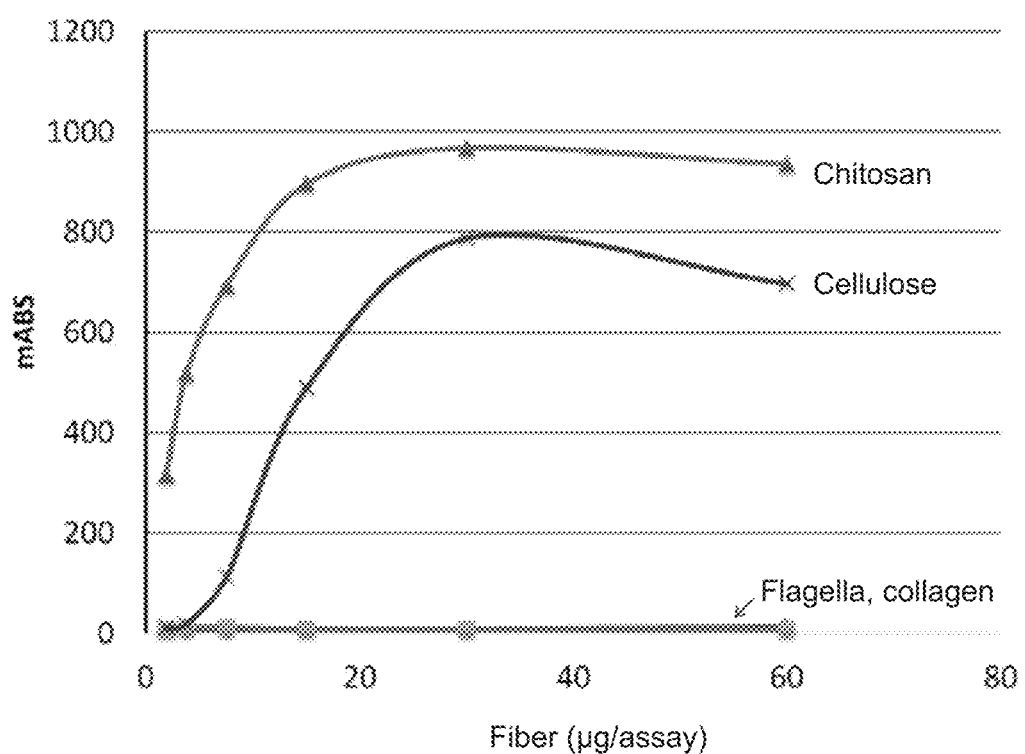
FIG. 27 is a diagram illustrating the strength of a band quantitatively determined by an immunochromatographic reader (Example 9).

Example 9 Comparison of Background Values in the Cases of Using Straight Chain Fiber and Branched Fiber Fiber solutions of flagella not having an antibody fixed thereon, collagen (manufactured by Jellyfish Research Laboratories, Inc.), chitosan (BiNFi-s8, manufactured by SUGINO MACHINE LIMITED) and cellulose (BiNFi-s5, manufactured by SUGINO MACHINE LIMITED) were adjusted with PBS so as to achieve the concentrations as shown in FIG. 26. 100 μl of each fiber solution, 100 μl of cal1 (0 μg/ml) among the same BNP standard solutions as in Example 1 and 20 μl of the BC23-11-fixed gold colloid obtained in Example 2 were mixed, and the respective mixtures were subjected to suction filtration through a 0.65 μm Durapore membrane filter using Bio-dot SF apparatus. The state of the gold colloid remaining on the membrane is shown in FIG. 26. Further, the color strength attributable to the gold colloid on the membrane was measured by an immunochromatographic reader, and the results are shown in FIG. 27. It was confirmed from the results that the background did not substantially increase even if the amount of the fiber used per assay was increased in the case of the straight chain fiber, however, in a case where the branched fiber was used, the background increased as the fiber amount was increased.

Example 10 Measurement System Using Electrospun Fiber (PVDF)

(1) Preparation of PVDF Short Nanofiber

PVDF (manufactured by SOLEF) was dissolved in DMF/acetone (60/40) at a concentration of 12.5 wt %, and using NANON-1 (manufactured by MECC CO., LTD.), and using a drum collector with a diameter of 200 rotating at 3,000 rpm, an oriented nanofiber was prepared by electrospinning (20 kV, 1.0 ml/hr). The fiber diameter was about 400 nm. The obtained nanofiber was cut at intervals of 100 μm to obtain a PVDF fiber having a length of 100 μm.

(2) Fixation of Antibody on PVDF Nanofiber

Figure 28:
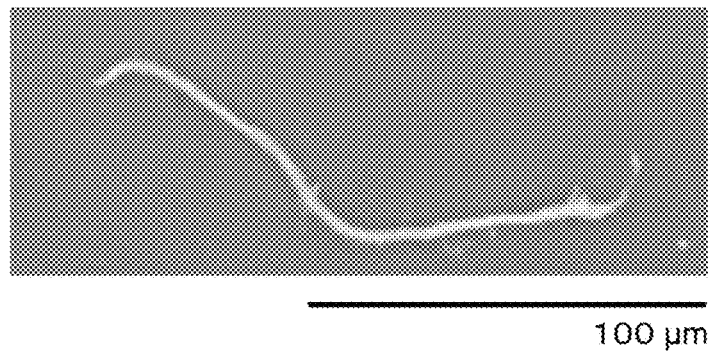
FIG. 28 is an electron micrograph of a short-chain nanofiber (Example 10).

The PVDF fiber was dispersed in methanol and subjected to centrifugal separation (15,000 rpm, 5 minutes) to obtain the PVDF fiber in the precipitates. The precipitates were dispersed in a 0.2M sodium carbonate buffer solution (pH 9.4) and subjected to centrifugal separation, and the supernatant was disposed of to remove methanol. Then, the pepsin-digested fragment ($F(ab')_2$) of BM33-28 prepared in Reference Example 3 was adjusted to have a concentration of 1 μg/ml (0.2M sodium carbonate buffer solution (pH 9.4)), and 1 ml thereof was added to the precipitates and left at rest at 4° C. overnight. An antibody not fixed on the fiber was removed by centrifugal separation (15,000 rpm, 5 minutes), and 1 mL of a 1% BSA solution (PBS) was added to the precipitates and left at rest at room temperature for one hour to conduct a blocking operation. Then, a washing operation with PBS was repeated three times, and 100 μl of PBS was added to obtain an antibody-bound PVDF fiber solution. The antibody-bound PVDF fiber was observed by a microscope (Miniscope TM-1000 manufactured by Hitachi Ltd.), and the obtained image is shown in FIG. 28.

(3) Detection of BNP

Figure 29:
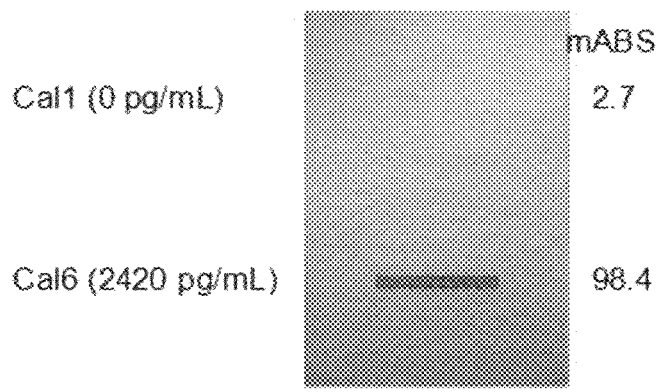
FIG. 29 is a photograph of a filter after a sample is filtrated and a diagram illustrating the strength of a band quantitatively determined by an immunochromatographic reader (Example 10).

Two sets of a solution obtained by mixing 20 μl of the antibody-bound PVDF fiber and 20 μl of the BC23-11-bound gold colloid obtained in Example 2 were prepared. 100 μl each of the same BNP standard solutions as in Example 1 were respectively added and left at rest for 5 minutes. Then, suction filtration through a 0.65 μm Durapore membrane filter was carried out using Bio-dot SF apparatus. The state of the gold colloid remaining on the membrane and the results of measurement by an immunochromatographic reader are shown in FIG. 29. It was confirmed from the results that the color strength attributable to the gold colloid increased by the presence of BNP. Thus, it was shown that the measurement system of the present invention can be constructed even in a case where a PVDF fiber was used.

Comparative Example 1 Detection of BNP Using Antibody-Bound Microparticles and Antibody-Fixed Gold Colloid (1) Fixation of BM33-28 on Microparticles To 100 µl of a suspension ($5.64 \times 10^{-1}$ pM) of white micropartides (particle size: 3 µm, surface modification: —$NH_2$, latex particles, manufactured by Micromer), 200 µl of 50 mM $KH_2PO_4$ (pH 8.0) was added. 5 µl of a DMSO solution of 250 mM SM(PEG)$_6$ (manufactured by Thermo) was added, followed by reaction at room temperature for 30 minutes to introduce maleimide groups to the surface of the microparticles, and centrifugal separation at 5,000 g for 10 minutes was repeated twice to remove an unreacted reagent.

Then, 500 µl of the BM33-28 Fab'-form antibody obtained in Example 2, adjusted to a concentration of 0.1 mg/ml (5 mM $KH_2PO_4$, pH 8.0) was added, followed by reaction at room temperature for 30 minutes. Then, 10 µl of 80 mM HS-PEG$_6$-OMe (manufactured by SIGMA-ALDRICH) was added to block unreacted maleimide groups, and then 100 µl of a 10% BSA solution was added to conduct blocking. Then, a washing operation with PBS was carried out twice to remove an unreacted antibody. The precipitates were suspended in 500 µl of a PBS buffer solution to obtain BM33-28-fixed microparticles.

(2) Detection of BNP

Figure 30:
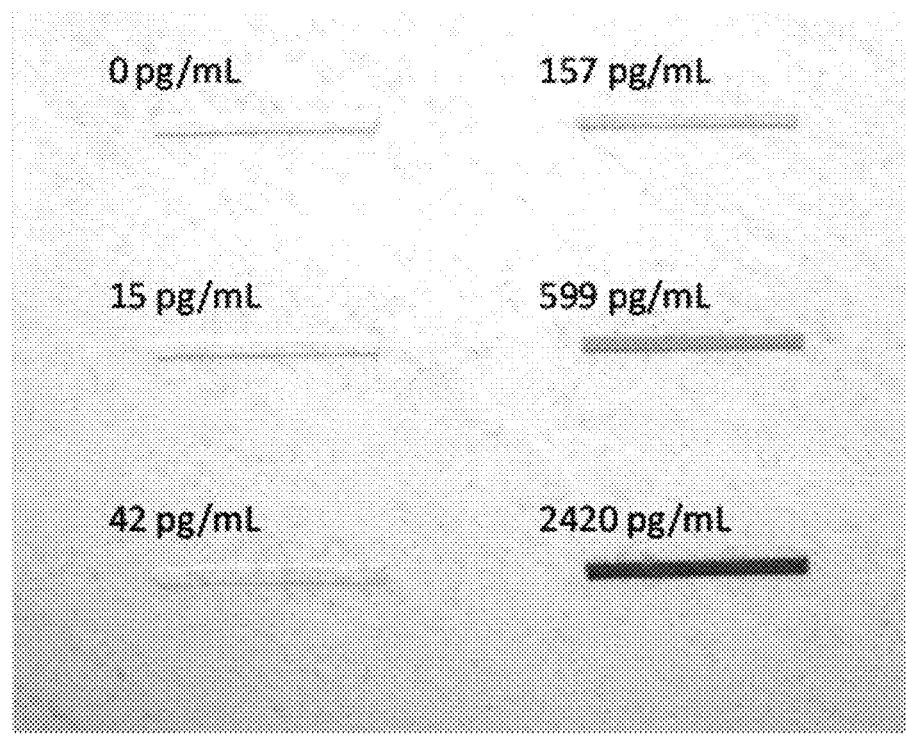
FIG. 30 is a photograph of a filter after a sample is filtrated (Comparative Example 1).
Figure 31:
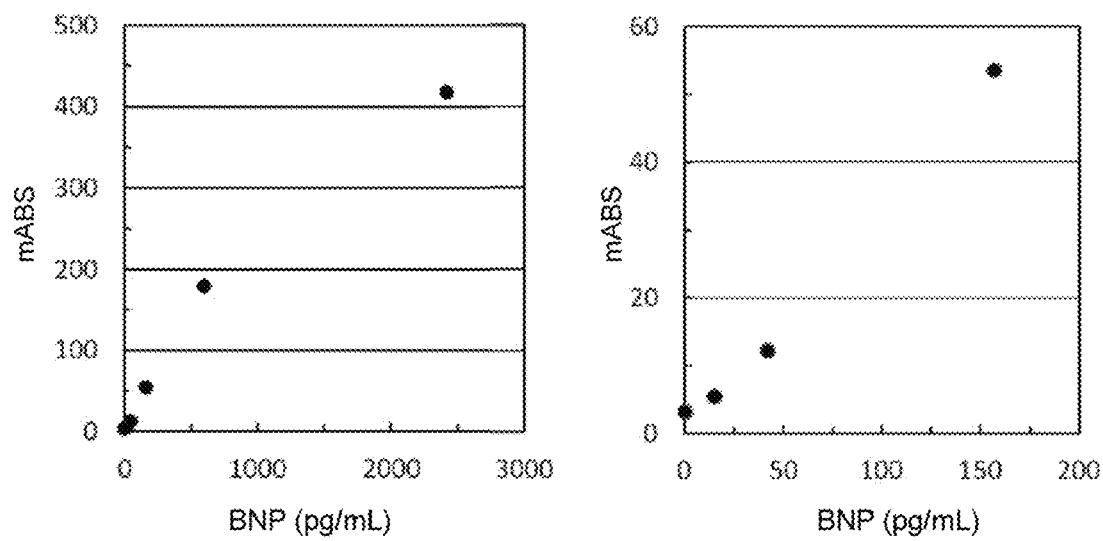
FIG. 31 is a diagram illustrating the strength of a band quantitatively determined by an immunochromatographic reader (Comparative Example 1).

20 µl of the BM33-28-fixed microparticles solution, 20 µl of the BC23-11-labeled gold colloid solution prepared in Example 2 and 210 µl of each of the same BNP standard solutions as in Example 2 were mixed and left at rest for 5 minutes. Then, suction filtration through a 0.65 µm Durapore membrane filter was carried out using Bio-dot SF apparatus. The state of the gold colloid remaining on the membrane is shown in FIG. 30. Further, the color strength attributable to the gold colloid on the membrane was measured by an immunochromatographic reader, and the results are shown in FIG. 31. It was confirmed from FIGS. 30 and 31 that the color strength attributable to the gold colloid increased in accordance with the concentration of BNP.

(3) Comparison of Data

The results of measurement of the color strength by an immunochromatographic reader by the assay using the flagella disclosed in Example 2 and by the assay in this Comparative Example are shown in Table 1.

TABLE 1

|  | cal1 | cal2 | cal3 | cal4 | cal5 | cal6 |
|---|---|---|---|---|---|---|
| BNP (pg/ml) | 0 | 15 | 42 | 157 | 599 | 2420 |
| Flagella (mABS) | 18.8 | 32 | 50.4 | 89.5 | 236.6 | 542.7 |
| Microparticles (mABS) | 3.3 | 5.5 | 12.2 | 53.5 | 179.9 | 418 |

Figure 32:
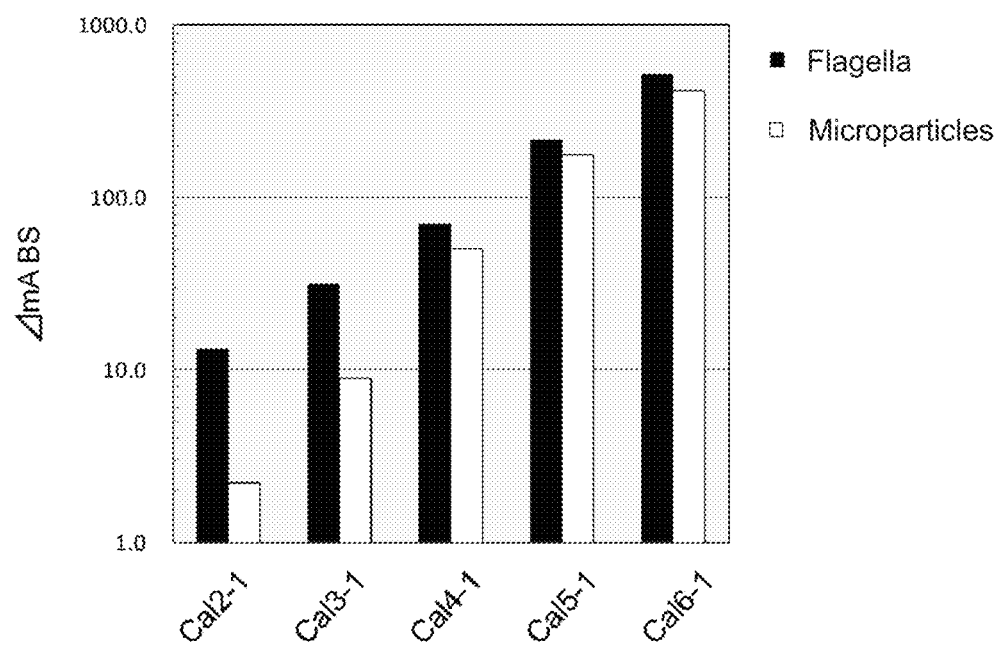
FIG. 32 is a diagram illustrating a difference in color strength between flagella and particles (Comparative Example 1).

The changes of the color strength of the assay systems using the flagella and the microparticles (changes of the color strength from cal1, ΔmABS) are calculated from Table 1 and the results are shown in FIG. 32. As a result, it was confirmed that AmABS is large in a low concentration region (cal2-1, cal3-1) in the assay system using a fiber (flagella) as compared with the assay system using microparticles. If AmABS is small, visual evaluation tends to be difficult. Accordingly, for application of the present invention, it was shown that use of a fiber is more preferred to use of microparticles.

The present invention has been described in detail with reference to specific embodiments, but, it is obvious for the person skilled in the art that various changes and modifications are possible without departing from the intension and the scope of the present invention.

The entire disclosures of Japanese Patent Application No. 2016-156775 filed on Aug. 9, 2016, Japanese Patent Application No. 2016-217584 filed on Nov. 7, 2016, Japanese Patent Application No. 2017-017706 filed on Feb. 2, 2017, Japanese Patent Application No. 2017-077086 filed on Apr. 7, 2017 and Japanese Patent Application No. 2017-102715 filed on May 24, 2017 including specifications, claims, drawings and summaries are incorporated herein by reference in their entireties.

The invention claimed is:

1. A method for detecting a substance to be detected, which comprises bringing
    a) a first recognizing substance bound to a fibrous substance,
    b) a second recognizing substance which is labeled, and
    c) a substance to be detected,
    provided that the first recognizing substance and the second recognizing substance are capable of being bound to the substance to be detected,
    into contact with one another in a dispersed state so as to form a complex in which the above a, b and c are bound together,
    separating the complex and an unbound b, and
    detecting the label of the obtained complex,
    wherein the fibrous substance has a diameter of from 1 to 500 nm and a length of from 100 nm to 50 μm,
    the fibrous substance does not include polyacrylonitrile, and
    the fibrous substance is a straight chain fiber.

2. The method according to claim 1, wherein the fibrous substance is a fiber constituted by self-organization or a polymer prepared by electrospinning.

3. The method according to claim 1, wherein the separation is conducted by filtration separation, centrifugal separation or electrophoresis.

4. The method according to claim 1, wherein the first recognizing substance and/or the second recognizing substance is an antibody against the substance to be detected.

5. The method according to claim 1, wherein the fibrous substance has a diameter of from 10 to 100 nm.

* * * * *